(12) United States Patent  
Knight et al.

(10) Patent No.: US 7,910,067 B2
(45) Date of Patent: Mar. 22, 2011

(54) SAMPLE TUBE HOLDER

(75) Inventors: Byron J. Knight, San Diego, CA (US); Mark A. Talmer, Pepperell, MA (US); Arthur G. Sandoval, San Francisco, CA (US); Robert A. Howard, Palo Alto, CA (US); Rommel M. Hipolito, San Diego, CA (US); Robert F. Scalese, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 1216 days.

(21) Appl. No.: 11/379,205

(22) Filed: Apr. 18, 2006

(65) Prior Publication Data

US 2006/0266719 A1    Nov. 30, 2006

Related U.S. Application Data

(60) Provisional application No. 60/672,609, filed on Apr. 19, 2005.

(51) Int. Cl.
*B01L 9/06* (2006.01)

(52) U.S. Cl. ....... 422/104; 211/71.01; 422/99; 422/300; 435/809

(58) Field of Classification Search ............. 422/104, 422/99, 300; 211/71.01; 435/809
See application file for complete search history.

(56) References Cited

U.S. PATENT DOCUMENTS

| | | | |
|---|---|---|---|
| 143,417 A | 10/1873 | Munroe | |
| 418,940 A | 1/1890 | Bray | |
| 1,168,535 A | 1/1916 | Moltrum | |
| 1,549,111 A | 8/1925 | Grollman | |
| 1,634,953 A | 7/1927 | McCune et al. | |
| D110,691 S | 8/1938 | Dudley | |
| 2,467,873 A | 4/1949 | Weir | |
| 2,708,037 A | 5/1955 | Planeta | |
| 2,741,913 A | 4/1956 | Dovas | |
| 2,902,170 A | 9/1959 | Miller | |
| 2,966,686 A | 10/1960 | Garey | |

(Continued)

FOREIGN PATENT DOCUMENTS

EP    0100663 A2    2/1984

(Continued)

OTHER PUBLICATIONS

PCT Search Report of the International Searching Authority for International Application No. PCT/US2006/014847, dated Nov. 11, 2006.

(Continued)

*Primary Examiner* — In Suk Bullock
*Assistant Examiner* — Paul S Hyun
(74) *Attorney, Agent, or Firm* — Charles B. Cappellari

(57) ABSTRACT

A sample tube holder having sample tube compartments with sets of spaced finger springs provided therein for maintaining sample tubes in substantially upright orientations. A guide structure having a series of openings is used to direct sample tubes into the sample tube compartments and to restrict lateral movement of sample tubes held thereby. A retainer is releasably engaged by the guide structure and has openings sized to provide access to sample tubes held by the sample tube compartments but which restrict vertical movement of the sample tubes. Tabs at a base of the sample tube holder and hold-downs fixed to a stationary structure adjacent a conveyor cooperate to restrict vertical movement of the sample tube holder during automated sampling procedures.

21 Claims, 20 Drawing Sheets

U.S. PATENT DOCUMENTS

| | | |
|---|---|---|
| 2,979,210 A | 4/1961 | Patterson |
| 3,072,362 A | 1/1963 | Allen |
| 3,109,084 A | 10/1963 | Walsh |
| 3,115,247 A | 12/1963 | Hauser |
| 3,142,385 A | 7/1964 | Kahlenberg |
| 3,175,695 A | 3/1965 | Goodman at al. |
| 3,186,556 A | 6/1965 | Forsstrom |
| 3,375,934 A | 4/1968 | Bates |
| 3,390,783 A | 7/1968 | Quackenbush, Jr. |
| 3,474,913 A | 10/1969 | Jungner et al. |
| D216,491 S | 1/1970 | Brown |
| 3,605,829 A | 9/1971 | Genese et al. |
| 3,643,812 A | 2/1972 | Mander et al. |
| 3,680,967 A | 8/1972 | Englehardt |
| 3,698,563 A | 10/1972 | Gordon et al. |
| 3,744,661 A | 7/1973 | Fischer, Jr. |
| 3,752,651 A | 8/1973 | Bush |
| 3,765,538 A | 10/1973 | Kowert |
| 3,785,773 A | 1/1974 | Rohrbaugh |
| RE28,165 E | 9/1974 | McCormick |
| 3,904,035 A | 9/1975 | Metzler et al. |
| 3,905,482 A | 9/1975 | Knulst |
| 3,905,772 A | 9/1975 | Hartnett et al. |
| 3,909,203 A | 9/1975 | Young et al. |
| 3,918,920 A | 11/1975 | Barber |
| 3,960,271 A | 6/1976 | Nelson |
| 4,036,391 A | 7/1977 | Prodel |
| 4,043,762 A | 8/1977 | Olds |
| 4,055,396 A | 10/1977 | Meyer et al. |
| 4,124,122 A | 11/1978 | Emmitt |
| 4,160,803 A | 7/1979 | Potts |
| 4,202,634 A | 5/1980 | Kraft et al. |
| 4,207,289 A | 6/1980 | Weiss |
| 4,265,855 A | 5/1981 | Mandle et al. |
| 4,284,603 A * | 8/1981 | Korom ........................ 422/101 |
| 4,287,155 A | 9/1981 | Tersteeg et al. |
| 4,322,216 A | 3/1982 | Lillig et al. |
| D265,126 S | 6/1982 | Beall |
| 4,391,780 A | 7/1983 | Boris |
| 4,407,943 A | 10/1983 | Cole et al. |
| 4,422,555 A | 12/1983 | Jacobs |
| 4,434,890 A | 3/1984 | Sieck et al. |
| 4,438,068 A | 3/1984 | Forrest |
| 4,495,150 A | 1/1985 | Cook et al. |
| 4,510,119 A | 4/1985 | Hevey |
| 4,522,089 A | 6/1985 | Alvi |
| D280,130 S | 8/1985 | Harkins et al. |
| 4,534,465 A | 8/1985 | Rothermel et al. |
| D286,912 S | 11/1986 | Andersen |
| 4,639,135 A | 1/1987 | Borer et al. |
| D290,401 S | 6/1987 | Bjorkman |
| 4,751,052 A | 6/1988 | Schwartz et al. |
| 4,761,268 A | 8/1988 | Andersen et al. |
| 4,787,523 A | 11/1988 | Kalous |
| 4,805,772 A | 2/1989 | Shaw et al. |
| 4,824,641 A | 4/1989 | Williams |
| 4,849,177 A | 7/1989 | Jordan |
| 4,895,650 A | 1/1990 | Wang |
| 4,932,533 A | 6/1990 | Collier |
| 4,933,147 A | 6/1990 | Hollar et al. |
| 4,948,564 A | 8/1990 | Root et al. |
| 4,963,493 A | 10/1990 | Daftsios |
| 4,982,850 A | 1/1991 | Mears |
| 5,004,103 A | 4/1991 | Connors et al. |
| 5,006,066 A | 4/1991 | Rouse |
| 5,029,699 A | 7/1991 | Insley et al. |
| 5,057,282 A | 10/1991 | Linder |
| 5,077,013 A | 12/1991 | Guigan |
| 5,080,232 A | 1/1992 | Leoncavallo et al. |
| 5,082,631 A | 1/1992 | Lenmark, Sr. et al. |
| 5,098,663 A | 3/1992 | Berthold et al. |
| 5,108,287 A | 4/1992 | Yee et al. |
| 5,127,541 A | 7/1992 | Wakatake |
| 5,128,105 A | 7/1992 | Berthold et al. |
| 5,133,939 A | 7/1992 | Mahe |
| 5,137,693 A | 8/1992 | Mawhirt |
| 5,169,603 A | 12/1992 | Landsberger |
| 5,173,265 A | 12/1992 | Golias et al. |
| D333,522 S | 2/1993 | Gianino |
| 5,186,339 A | 2/1993 | Heissler |
| 5,191,975 A | 3/1993 | Pezzoli et al. |
| D336,219 S | 6/1993 | Held |
| 5,217,694 A | 6/1993 | Gibler et al. |
| 5,232,669 A | 8/1993 | Pardinas |
| 5,318,753 A | 6/1994 | Honda |
| 5,322,668 A | 6/1994 | Tomasso |
| 5,324,481 A | 6/1994 | Dunn et al. |
| 5,350,564 A | 9/1994 | Mazza et al. |
| 5,378,433 A | 1/1995 | Duckett et al. |
| 5,456,360 A | 10/1995 | Griffin |
| 5,456,882 A | 10/1995 | Covain |
| 5,472,669 A | 12/1995 | Miki et al. |
| 5,533,700 A | 7/1996 | Porter |
| 5,571,481 A | 11/1996 | Powell et al. |
| 5,579,928 A | 12/1996 | Anukwuem |
| 5,605,160 A * | 2/1997 | Fishman ....................... 600/556 |
| 5,632,388 A | 5/1997 | Morrison et al. |
| 5,642,816 A | 7/1997 | Kelly et al. |
| 5,650,125 A | 7/1997 | Bosanquet |
| 5,651,941 A | 7/1997 | Stark et al. |
| 5,687,849 A | 11/1997 | Borenstein et al. |
| 5,700,429 A | 12/1997 | Buhler et al. |
| 5,704,495 A | 1/1998 | Bale et al. |
| 5,777,303 A | 7/1998 | Berney |
| D405,192 S | 2/1999 | Smith et al. |
| 5,897,090 A | 4/1999 | Smith et al. |
| 5,916,527 A | 6/1999 | Haswell |
| 5,931,318 A | 8/1999 | Shauo |
| D413,677 S | 9/1999 | Dumitrescu et al. |
| D414,273 S | 9/1999 | Smith et al. |
| 5,959,221 A | 9/1999 | Boyd et al. |
| D417,009 S | 11/1999 | Boyd |
| 5,985,219 A | 11/1999 | Lind |
| 5,993,745 A | 11/1999 | Laska |
| 5,996,818 A | 12/1999 | Boje et al. |
| 6,015,534 A | 1/2000 | Atwood |
| D420,747 S | 2/2000 | Dumitrescu et al. |
| D421,130 S | 2/2000 | Cohen et al. |
| 6,027,691 A | 2/2000 | Watts et al. |
| 6,065,617 A | 5/2000 | Cohen et al. |
| 6,123,205 A | 9/2000 | Dumitrescu et al. |
| D433,759 S | 11/2000 | Mathis et al. |
| 6,156,275 A | 12/2000 | Dumitrescu et al. |
| 6,190,619 B1 | 2/2001 | Kilcoin et al. |
| 6,193,064 B1 | 2/2001 | Finneran |
| D439,673 S | 3/2001 | Brophy et al. |
| 6,221,317 B1 | 4/2001 | Carl |
| 6,235,245 B1 | 5/2001 | Sherman et al. |
| 6,274,092 B1 | 8/2001 | Itoh |
| 6,335,166 B1 | 1/2002 | Ammann et al. |
| 6,618,981 B1 | 9/2003 | Rodriguez |
| 7,132,082 B2 | 11/2006 | Aviles et al. |
| 2002/0021983 A1 | 2/2002 | Comte et al. |
| 2002/0108917 A1 | 8/2002 | Maruyama |
| 2003/0017084 A1 | 1/2003 | Dale et al. |
| 2003/0215365 A1 | 11/2003 | Sevigny et al. |
| 2004/0124109 A1 | 7/2004 | Hassinen et al. |
| 2004/0195193 A1 | 10/2004 | Jafari et al. |
| 2005/0180895 A1* | 8/2005 | Itoh .............................. 422/104 |

FOREIGN PATENT DOCUMENTS

| | | | |
|---|---|---|---|
| EP | 0219802 | A2 | 4/1987 |
| EP | 0414644 | A | 2/1991 |
| EP | 0919281 | A2 | 6/1999 |
| EP | 0965385 | A2 | 12/1999 |
| GB | 2064998 | A | 6/1981 |
| JP | 1-161154 | | 6/1989 |
| WO | WO93/01739 | A1 | 2/1993 |

OTHER PUBLICATIONS

PCT Written Opinion of the International Searching Authority for International Application No. PCT/US2006/014847, dated Mar. 30, 2007.

AIPO Office Action, Australian Patent Application No. 2006236263, Nov. 3, 2010.

* cited by examiner

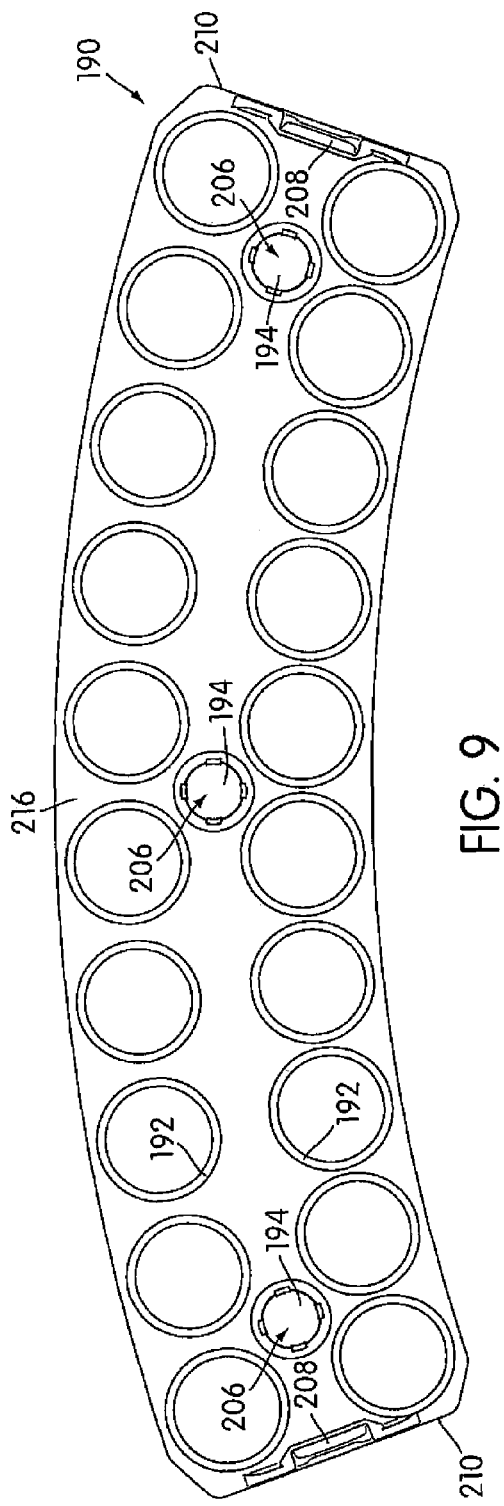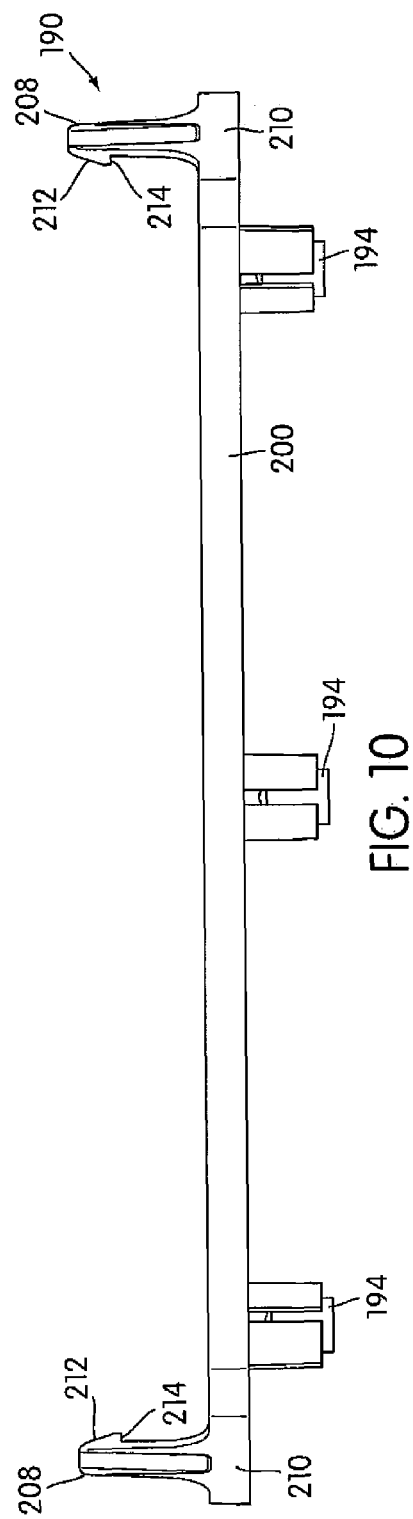

SAMPLE TUBE HOLDER

CROSS-REFERENCE TO RELATED APPLICATIONS

This application claims the benefit of U.S. Provisional Application No. 60/672,609, filed Apr. 19, 2005, the contents of which are hereby incorporated by reference herein.

FIELD OF THE INVENTION

The present invention relates to a sample tube holder for holding, aligning and/or retaining a plurality of sample tubes. The sample tube holder of the present invention is especially suited for use with an automated sampling system and sample tubes having penetrable closure devices.

BACKGROUND OF THE INVENTION

Automated analyzers are in common use today for assaying the contents of sample tubes for a variety of purposes. Conveyors are often included in these automated analyzers for transporting sample tubes to fluid transfer stations, where robotic pipettors, or other fluid transfer devices, transfer materials to or from the sample tubes. To ensure that materials are being accurately transferred by robotic pipettors, it is important that sample tubes being conveyed within an analyzer be maintained in substantially upright orientations. Additionally, for applications in which robotic pipettors are used to pierce penetrable closure devices associated with the sample tubes, it is also important that holders for carrying the sample tubes are also capable of retaining the sample tubes, as it is possible for the retaining forces of a closure device to exceed the withdrawal forces of a robotic pipettor, thereby resulting in the removal of a sample tube. Removal of a sample tube will interrupt the workflow of a laboratory and could result in the loss of a sample or, worse, contamination of an analyzer.

SUMMARY OF THE INVENTION

The present invention provides a sample tube holder for holding and aligning a plurality of sample tubes that is particularly suited for use with an automated analyzer having a robotic pipettor. The sample tube holder of the present invention has a base, a first sample tube holding structure that is positioned above and structurally interrelated to the base, and a second sample tube holding structure that is positioned above and structurally interrelated to the first sample tube holding structure. Each of the sample tube holding structures has a series of openings and a set of spaced-apart finger springs depending inwardly from about each opening, where the openings of the first sample tube holding structure are coaxially aligned with the openings of the second sample tube holding structure. The openings are sized to receive sample tubes therethrough and are preferably formed in a generally planar member of each of the sample tube holding structures (e.g., plates). The finger springs preferably depend from bottom surfaces of the generally planar members of the sample tube holding structures, and each set of finger springs is configured and arranged to frictionally hold a sample tube therebetween, preferably in a substantially upright position for sampling with a robotic pipettor.

For uses in which sample tube containment presents a problem, such as applications involving the use sample tubes having penetrable caps, where the frictional forces between a penetrable cap and a fluid transfer device used to penetrate the cap may result in the unintended removal of a sample tube, the sample tube holder preferably includes a guide structure and a retainer which is releasably engaged by the guide structure. The guide structure is positioned above and structurally interrelated to the second sample tube holding structure and includes a series of openings, where each opening of the guide structure is coaxially aligned with an aligned set of openings in the first and second sample tube holding structures and is sized to receive a sample tube therethrough. The retainer has a series of openings, where each opening of the retainer is coaxially aligned with one of the openings in the guide structure and is sized to block the passage of a sample tube therethrough. The openings in the guide structure and retainer are preferably formed in generally planar members (e.g., plates).

As used herein, the phrase "structurally interrelated" means that the referred to structures may be joined directly or indirectly to each other. The term "indirectly" is used herein to mean that there is intervening structure connecting the structures being joined.

The openings in the sample tube holding structures, guide structure and/or retainer may constitute a single set of aligned, spaced openings or, more preferably, they may constitute two or more sets of aligned, spaced openings. In a particularly preferred embodiment, two sets of generally parallel openings are formed in each of the plates to allow for parallel processing of samples.

In one embodiment of the present invention, a spacer is included for joining the first sample tube holding structure to the second sample tube holding structure. By providing spatial separation between the finger springs of the first and second sample tube holding structures, the spacer aids in maintaining sample tubes held by the sample tube holder in substantially upright orientations. A particularly preferred spacer of the present invention defines a series of chambers, where each chamber is aligned with and extends between a set of aligned openings in the first and second sample tube holding structures. Each chamber of the spacer is sized to receive a sample tube therein.

In another embodiment of the present invention, a series of partitions extend upward from the base and divide the base into a plurality of sample tube receiving wells. Each sample tube receiving well is located beneath a chamber of the spacer and a corresponding, aligned set of openings in the first and second sample tube holding structures to collectively form a sample tube compartment. The sample tube compartments function to isolate the sample tubes from each other and help to prevent carryover contamination between the sample tubes. Each sample tube compartment preferably has a slot formed therein to permit viewing of machine readable information (e.g., scannable bar code) affixed to an opposed surface of the chamber and/or to a sample tube which is contained within the sample tube compartment. Machine readable information affixed to a surface of the chamber and visible through the slot can be used to determine whether a sample tube is present in the chamber (i.e., the machine readable information is blocked and cannot be detected by a reader or scanner when the sample tube is present), and machine readable information affixed to a surface of the sample tube and visible through the slot may provide patient identification and/or testing information.

Each finger spring of the present invention includes an arm portion and an end portion. The arm portions of the finger springs may have, for example, a curved or flat surface in cross-section and are preferably bowed, extending downward and inward from bases about the openings formed in the first and second sample tube holding structures. So that the finger springs bend more uniformly as sample tubes are inserted through sets of finger springs, and to reduce stress at the bases, the arm portions preferably have a hollowed out back side and decrease in size moving in the direction of the end portions from the bases. The end portions of the finger springs preferably have contoured surfaces that provide one or more points of contact with the sample tubes they hold. For example, the end portions of the finger springs may be convexly shaped to permit a single point of contact with the sample tubes or they may be flared, thereby providing continuous contact or multiple points of contact with the sample tubes. Convexly shaped end portions best facilitate the insertion and removal of sample tubes, while end portions having continuous contact or multiple points of contact with the sample tubes may add stability and reduce the number of finger springs needed to maintain the sample tubes in generally upright orientations. To allow for the smooth insertion of flat-bottomed sample tubes, the transition from the arm portion to the end portion of each finger spring is preferably smoothly contoured.

Sets of aligned finger springs in the first and second sample tube holding structures are spaced from each other to maximize the vertical stability of sample tubes held by the sample tube holder. The location of the first sample tube holding structure relative to the base is preferably such that the end portions of finger springs depending from the first sample tube holding structure contact generally parallel sections of closed side walls of the sample tubes rather than contoured bottom portions (e.g., rounded or frustoconical bottom portions) which could affect the vertical stability of the sample tubes. The sizes of the openings in the first and second sample tube holding structures and, accordingly, the extent to which the members of each set of finger springs are spaced from each other is determined by the sample tube diameters intended for use with the sample tube holder. Logically, the spacing between finger springs must be tailored to accommodate the largest diameter sample tubes intended for use with the sample tube holder, as well as allow the end portions of the finger springs to contact and be deflected by the smallest diameter sample tubes contemplated for use. The finger springs are preferably oriented to allow an unobstructed view of machine readable information affixed to the spacer or sample tubes contained within the sample tube compartments. Preferred finger spring sets include four finger springs, although fewer or more finger springs may be used, depending upon the positions and uses of the finger springs, as well as the shapes of the end portions (e.g., fewer finger springs may be required where the end portions have continuous contact or multiple points of contact with sample tubes).

The openings in the guide structure of the preferred embodiment of the present invention are preferably located so that at least a portion of a closed side wall of a cap joined to each sample tube is contained within a closed wall defining one of the openings when the sample tubes are fully inserted into the sample tube holder (i.e., closed bottom ends of the sample tubes contact the base). Ideally, when a portion of a cap is contained within an opening in the guide structure, the longitudinal axis of the cap deviates from the longitudinal axis of a fluid transfer device (e.g., pipette tip) penetrating the cap by no more than about 0.10 inches (2.54 mm), and the longitudinal axis of the cap deviates from the longitudinal axis of the opening by no more than about 0.020 inches (0.508 mm). The amount of deviation permissible will, of course, depend upon the size of the fluid transfer device and the opening in the cap. Accurately centering the caps prior to piercing them with a robotic pipetting device may limit the force required to penetrate the caps and, accordingly, can provide for more accurate pipetting.

A latch system is preferably used to join the retainer to the guide structure, although other fasteners, such as screws or clips, may be used. In the preferred embodiment, a pair of latches extends upward from the guide structure and engages notches formed on a top surface of the retainer to maintain the retainer in fixed position relative to the guide structure. The latches and the notches are preferably located at the ends of the guide structure and retainer, respectively. The retainer can be released from the guide structure by manually pushing outward on the top ends of the latches. While the retainer is preferably detachable from the guide structure (i.e., no structural connection), the retainer may also be joined to the guide structure by other means, such as a hinge or hinges to pivotally mount the retainer on the guide structure and fasteners to hold the retainer in a fixed position during use.

In an alternative embodiment of the present invention, a sample tube holder is provided that includes a base defining a series of sample tube compartments for receiving and holding a plurality of sample tubes in substantially upright orientations. To hold the sample tubes in substantially upright orientations, each sample tube compartment may comprise, by way of example, a slot conforming to the dimensions of a particular sample tube or a spring or set of spaced, inwardly depending finger springs. This sample tube holder further includes a guide structure and a retainer substantially as described hereinabove, where the guide structure is positioned above and structurally interrelated to the base and each opening in the guide structure is aligned with one of the sample tube compartments.

A further embodiment of the present invention solves the problem of sample tube holders being lifted from automated conveyors during sampling procedures by including a tab or series of tabs which extend laterally outward from each side of the base. The tab or tabs are configured and located to move freely beneath at least a pair of hold-downs positioned on opposite sides of the sample tube holder as the sample tube holder is being moved into an automated pipetting station on a conveyor, such as a carousel or belt. The hold-downs are fixed to a stationary structure adjacent the conveyor and will engage the sample tube holder if the sample tube holder is lifted during an automated pipetting step to prevent it from being removed from the conveyor. Lifting of the sample tube holder is most likely to occur if the material of a penetrable cap of a sample tube held by the sample tube holder binds a pipettor or pipette tip associated with an automated pipetting station as it is being withdrawn from the sample tube. Examples of penetrable caps are disclosed by Anderson et al. in U.S. Pat. No. 6,716,396 and Kacian et al. in U.S. Pat. No. 6,893,612, the contents of each of which patents is hereby incorporated by reference herein. An example of an automated pipetting station and conveyor for use in performing nucleic acid-based detection assays is disclosed by Ammann et al. in U.S. Pat. No. 6,335,166 (the contents of which are hereby incorporated by reference herein), a commercial embodiment of which is available from Gen-Probe Incorporated as the TIGRIS DTS® System.

In yet another embodiment of the present invention, a method is provided for conveying the same tube holder of any of the above-described embodiments into a pipetting station and drawing sample material from a sample tube held by the sample tube holder with a fluid transfer device, such as a pipette tip, using an automated pipettor in the pipetting station. In a particularly preferred embodiment, the fluid transfer device of the automated pipettor pierces a penetrable cap of the sample tube, and the fluid transfer device is removed from the sample tube without removing the sample tube from the sample tube holder. The material withdrawn from the sample tube may be subjected to analysis, such as interrogating the sample for a particular chemical or biological component. Particularly preferred is a nucleic acid-based assay for detecting the presence of a target sequence indicative of the presence of a particular organism or virus in the sample material. See, e.g., Kohne in U.S. Pat. No. 5,641,631. To increase the sensitivity of such an assay, an amplification step for increasing the copy number of a target sequence may be desired. Numerous amplification procedures are described in Nucleic Acid Amplification Technologies, H. H. Lee et al., 1997, Birkhäuser Boston, ISBN 0-8176-3921-7.

The sample tube holders of the present invention may have, for example, a rectilinear or an curvilinear shape, although a curvilinear shape is particularly preferred. The sample tube holders preferably have a curvilinear shape to accommodate their use on an automated sample carousel, such as the carousel disclosed by Ammann et al. in U.S. Pat. No. 6,335,166.

These and other features, aspects, and advantages of the present invention will become apparent to those skilled in the art after considering the following detailed description, appended claims and accompanying drawings.

BRIEF DESCRIPTION OF THE DRAWINGS

FIG. 9 is a top view of a guide structure of the sample tube holder of FIG. 1.

FIG. 10 is a side view of the guide structure of FIG. 9.

Figure 1:
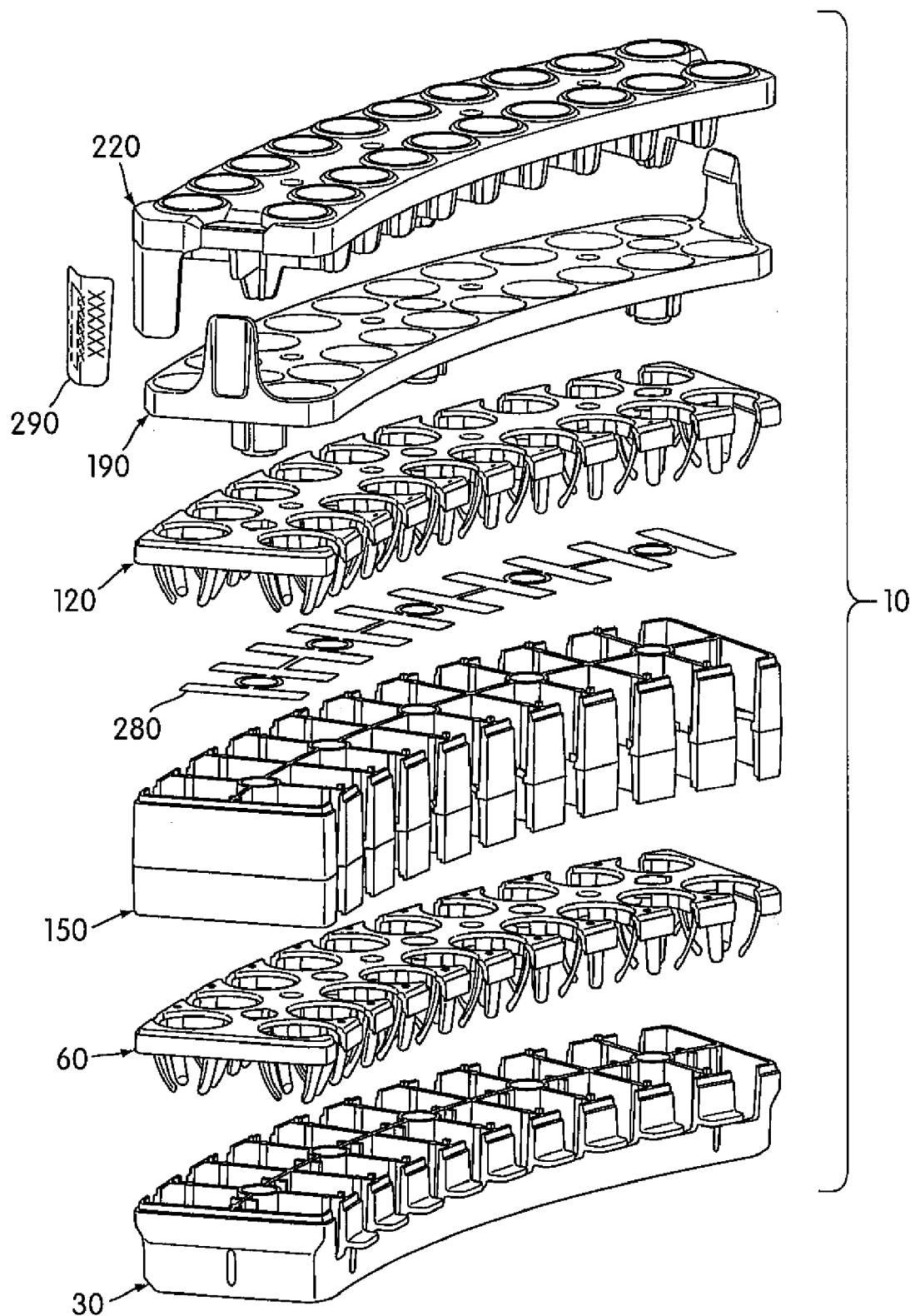
FIG. 1 is an exploded perspective view of a preferred sample tube holder according to the present invention.

The sample tube holders illustrated in the attached drawings include a number of redundant features. Where it would be clear to those skilled in the art from reviewing the drawings and reading the following description what features are being shown, the inventors have attempted to avoid including an excessive number of reference numbers by providing reference numbers for only a representative number of similar features depicted therein.

DETAILED DESCRIPTION OF THE PREFERRED EMBODIMENTS

While the present invention may be embodied in a variety of forms, the following description and accompanying drawings are merely intended to disclose some of those forms as specific examples of the present invention. Accordingly, the present invention is not intended to be limited to the forms or embodiments so described and illustrated. Instead, the full scope of the present invention is set forth in the appended claims.

With reference to the figures, a preferred sample tube holder 10 of the present invention is shown for holding sample tubes 300 and for limiting vertical movement of the sample tube holder when material is being removed from the sample tubes. Sample tube holders 10 of the present invention are preferably used in combination with sample tubes 300 having sealed caps 310 which can be penetrated by plastic pipette tips using an automated pipetting system. A preferred pipetting system for use with the sample tube holders 10 is the Robotic Sample Processor, Model No. RSP9000, available from Cavro Inc. of Sunnyvale, Calif. (As described herein, the sample tube holders of the present invention can also be adapted for use with uncapped sample tubes.) To ensure proper alignment for piercing the penetrable caps 310 and withdrawing sample, the sample tube holders 10 of the present invention substantially immobilize the sample tubes 300 they carry, thereby restricting both vertical and lateral movement of the sample tubes during sampling procedures. The sample tubes 300 used with the sample tube holders 10 of the present invention may be transport tubes provided with sample collection kits which are used to receive and store samples for shipping and future analysis, including analysis with nucleic acid-based assays or immunoassays diagnostic for a particular pathogenic organism or virus. Such samples may include, for example, blood, urine, saliva, sputum, mucous or other bodily secretion, pus, amniotic fluid, cerebrospinal fluid, seminal fluid, tissue specimens, stool, environmental samples, food products, chemicals, powders, particles or granules. The sample tubes 300 may be of any shape or composition, provided receptacle components 320 of the sample tubes are shaped to receive and retain the material of interest (e.g., animal, environmental, industrial, food or water samples). The vessel component 320 includes a closed end and an open end adapted for fixing the cap 310 thereto (e.g., mated helical threads). Preferred sample tubes are disclosed by Anderson et al. in U.S. Pat. No. 6,716,396 and by Kacian et al. in U.S. Pat. No. 6,893,612. It is typically important that the composition of the sample tube 300 be essentially inert relative to the sample so that it does not significantly interfere with the performance or alter the results of an assay.

The sample tube holders 10 of the present invention may be of any general shape, but preferably have a rectilinear or an curvilinear shape adapted for use on an automated conveyor. The components of the sample tube holders 10 can be formed using techniques which are well known to those skilled in the art of injection molding. The preferred material used to mold the components of the sample tube holders 10 is polyethersulfone (PES) with 15% glass fiber, which is available as Product No. RTP 1402 from the RTP Company of Winona, Minn.

As illustrated in FIG. 1, a particularly preferred sample tube holder 10 according to the present invention includes a base 30, a first finger spring plate 60 positioned above and joined to the base, a second finger spring plate 120, a spacer 150 which separates and indirectly joins the second finger plate to the first finger spring plate, a guide structure 190 positioned above and joined to second finger spring plate, and a retainer 220 positioned above and releasably engaged by the guide structure. Each of the finger spring plates 60, 120 of this sample tube holder 10 has two, parallel rows of spaced-apart openings 62, 122 with a set of four spaced-apart finger springs 100 (reference number "100" refers to either of the illustrated finger spring embodiments identified by reference numbers "100a" and "100b" in the figures) depending from a bottom surface 64, 124 of the finger spring plates about the periphery of the openings.

Figure 2:
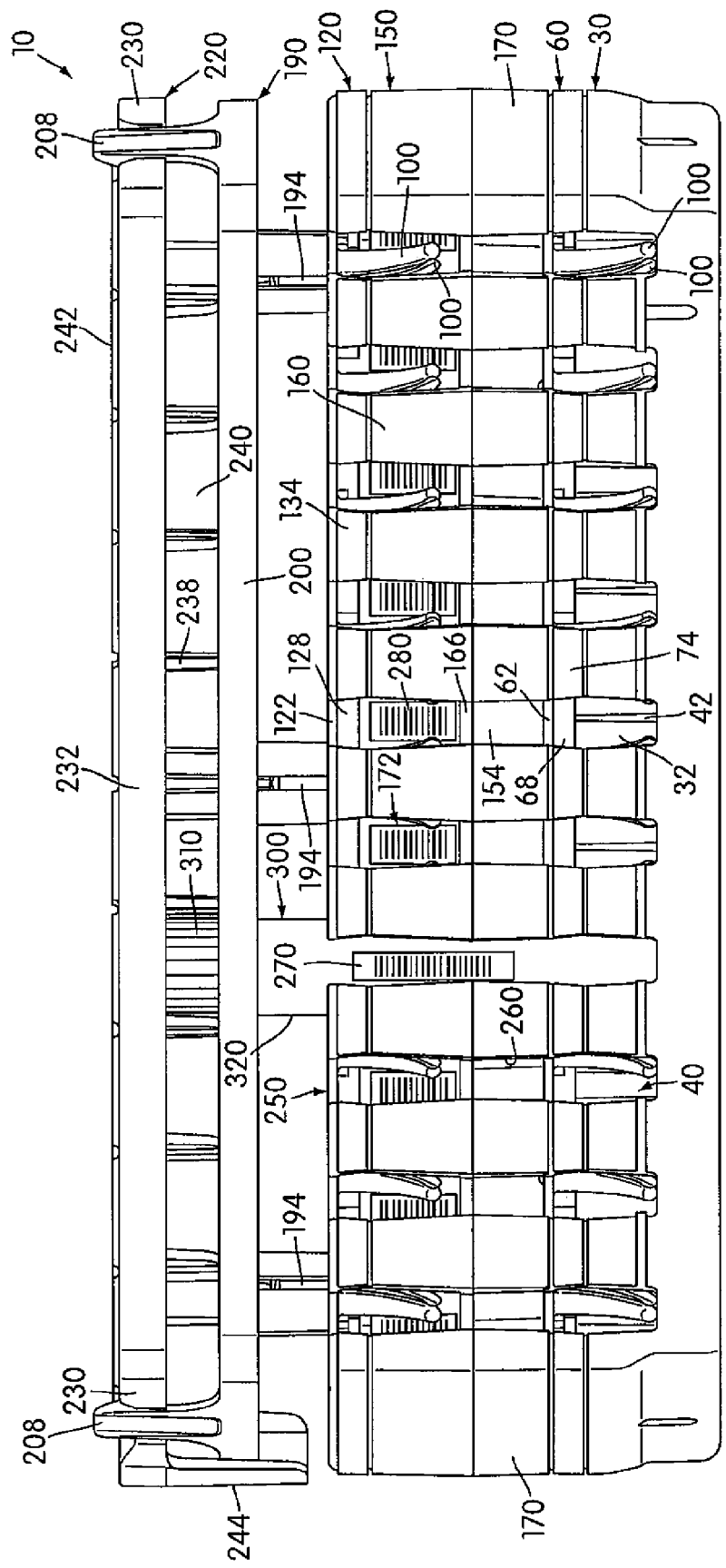
FIG. 2 is an elevation side view of the sample tube holder of FIG. 1.
Figure 3:
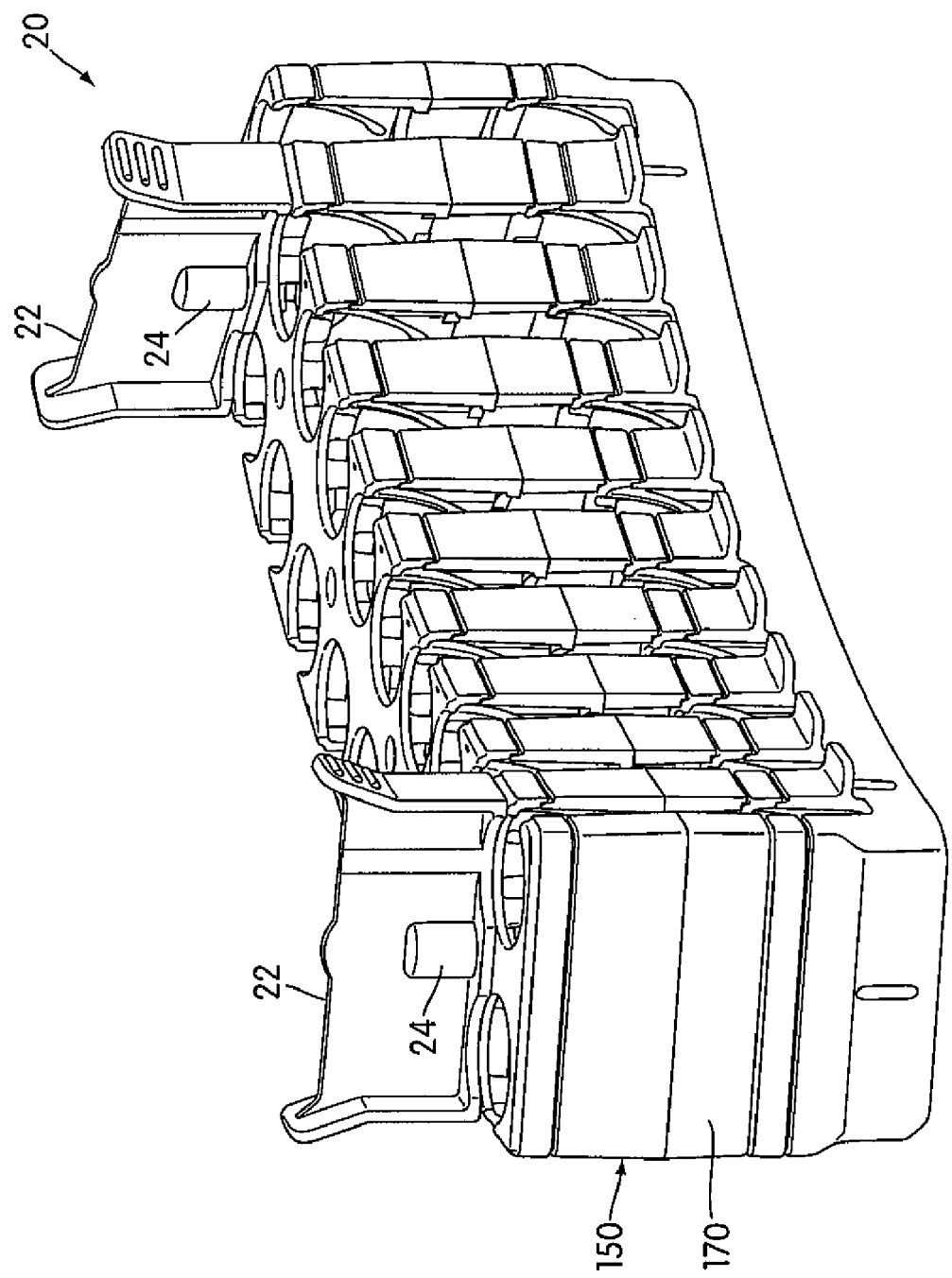
FIG. 3 is a perspective view of another sample tube holder according to the present invention.

In an alternative embodiment illustrated in FIG. 3, a sample tube holder 20 is shown which shares all of the features of the sample tube holder 10 shown in FIGS. 1 and 2, except for the guide structure 190 and the retainer 220. This embodiment is particularly useful for applications in which open-ended sample tubes are not sealed with a cap or other closure device, but must be maintained in a substantially vertical orientation to ensure accurate pipetting with a robotic pipetting device. One noticeable addition to the alternative sample tube holder 20 is a pair of finger grips 22 which are joined to and extend upward from the second finger spring plate 120. The finger grips 22 also include bosses 24 sized to receive and hold assembly screws (not shown), as discussed below. Except for the guide structure 190 and the retainer 220, the continuing structural discussion of the preferred sample tube holder 10 applies equally to the alternative sample tube holder 20 illustrated in FIG. 3.

In practice, sample tubes 300 are inserted through tapered openings 192 in the guide structure 190 shown in FIG. 9 and into sample tube compartments 250 depicted in FIG. 2. Each opening 192 in the guide structure 190 is coaxially aligned with a set of openings 62, 122 in the first and second finger spring plates 60, 120, and each of the openings 62, 122, 192 is sized to accommodate the sample tube 300 having the largest diameter intended for use with the sample tube holder 10. The openings 62, 122, 192 may of the same or different sizes.

Figure 4:
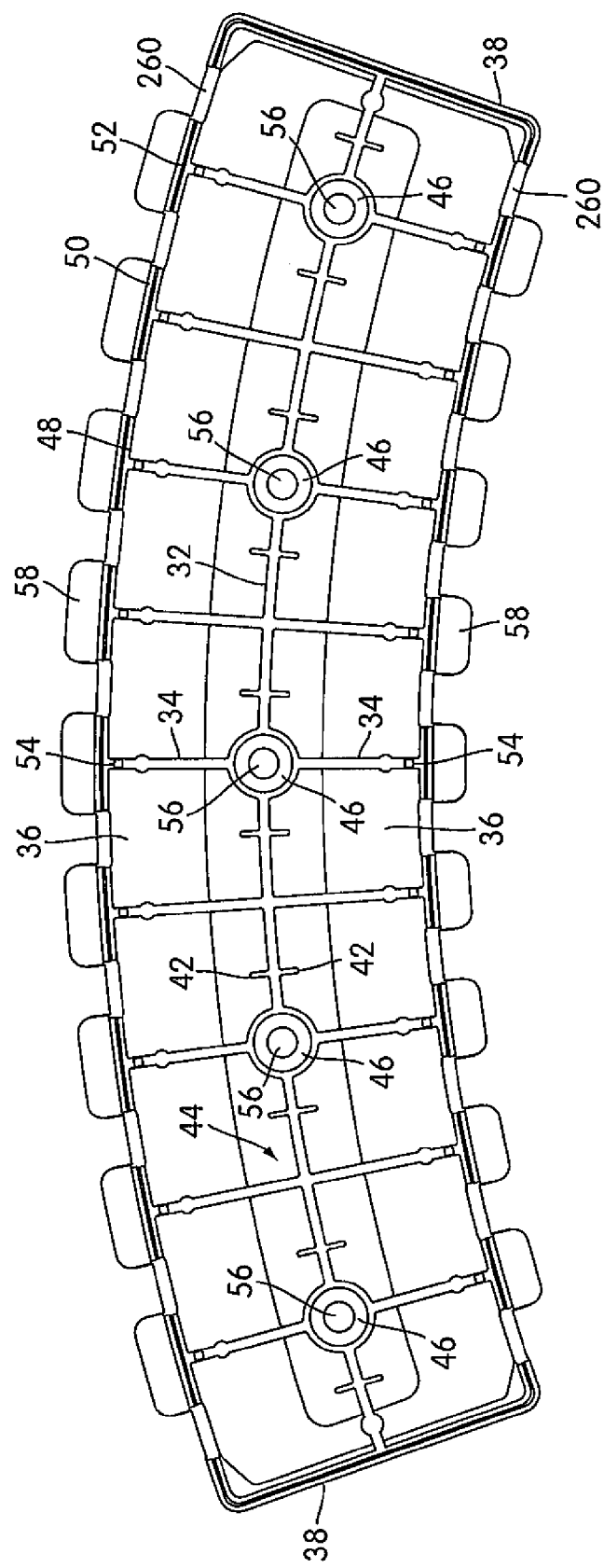
FIG. 4 is a top view of a base of the sample tube holder of FIG. 1.

Each sample tube compartment 250 is defined by a generally enclosed space beneath each opening 192 in the guide structure 190 and between the base 30 and the second finger spring plate 120. Starting from the base 30, FIG. 4 shows that the base includes a dividing wall 32 and a series of spaced-apart partitions 34 extending laterally or radially outward from the dividing wall and upward from a floor 36, as well as a pair of end walls 38, which define a set of wells 40 for receiving the closed bottom ends of the sample tubes 300. A series of spaced-apart ribs 42 also extend laterally or radially outward from the dividing wall 32 and into the wells 40 to provide the base 30 with added strength. Openings 44 in the floor 36 of the base 30 are included to drain solutions used to clean the sample tube holders 10 at the conclusion of an assay. One such solution is a 50% bleach solution (i.e., a bleach solution containing about 5% to about 6.5% (w/v) sodium hypochlorite) used to degrade nucleic acids which may be present on the sample tube holder 10 following sampling for a nucleic acid-based amplification assay. See GEN-PROBE® APTIMA COMBO 2® Assay Package Insert, IN0037 Rev. A/2003-08.

Figure 6:
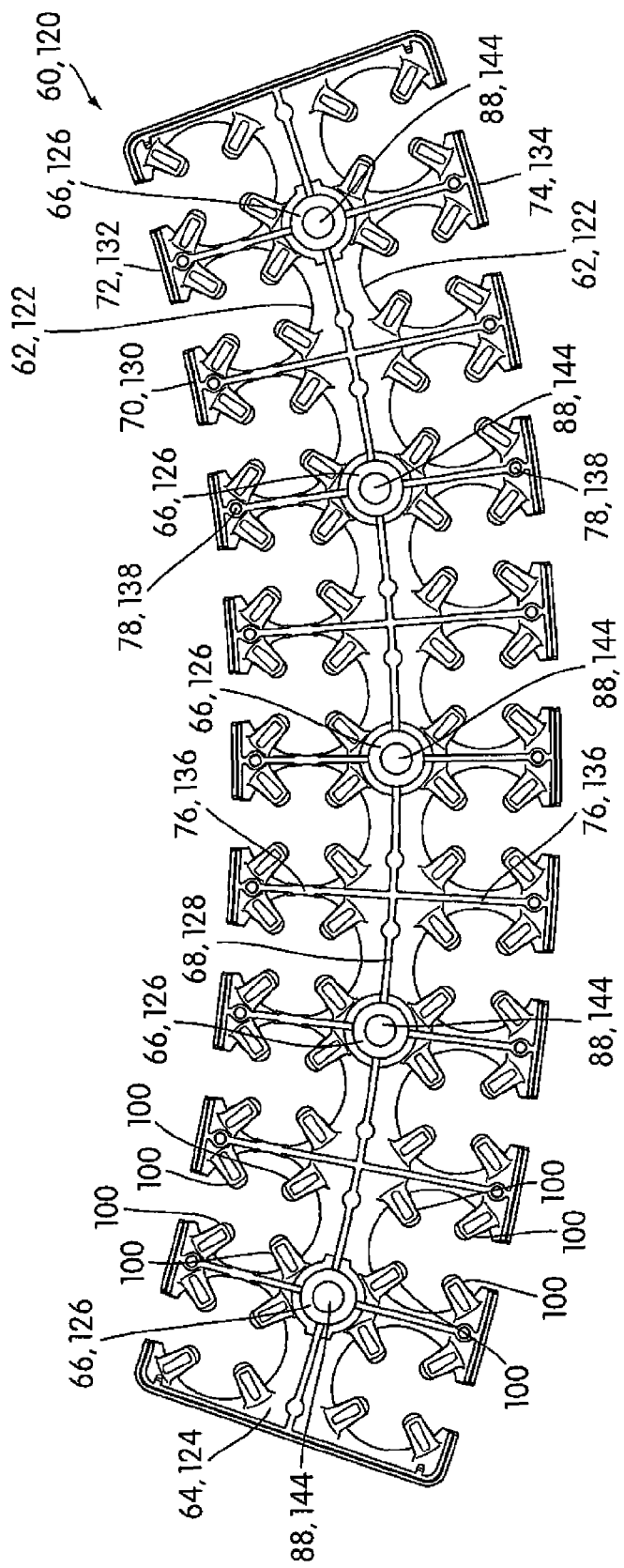
FIG. 6 is a bottom view of the finger spring plate of FIG. 5.

FIG. 6 shows a series of spaced-apart bosses 66 depending from along a dividing wall 68 of the first finger spring plate 60 for registering the first finger spring plate on the base 30 using mated recesses 46 along the dividing wall 32 of the base depicted in FIG. 4. A shoulder 48 extending about a top surface 50 of a side wall 52 of the base 30 also registers with a mated lower shoulder 70 extending about a bottom surface 72 of a side wall 74 of the first finger spring plate 60. Engagement of the mated shoulders 48, 70 of the base 30 and first finger spring plate 60 helps to restrict flexing of the first finger spring plate. To further prevent undesired flexing of the first finger spring plate 60, partitions 76 depending from the bottom surface 64 of the first finger spring plate include receiving holes 78 adjacent the side wall 74 which register with protuberances 54 extending upward from the partitions 34 in the base 30 adjacent the side wall 52. When the first finger spring plate 60 is joined to the base 30, the dividing walls 32, 68 and partitions 34, 76 of the base 30 and the first finger spring plate 60 are generally in touching contact and, thereby, further define the generally enclosed sample tube compartments 250.

Figure 5:
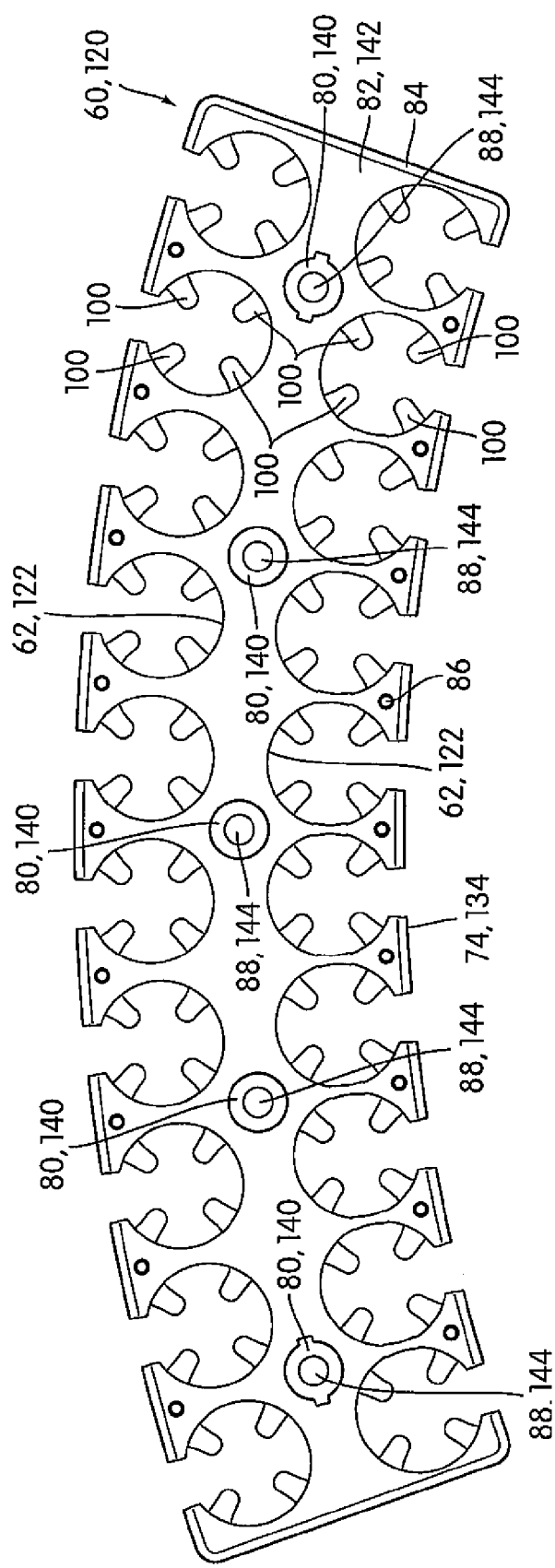
FIG. 5 is a top view of a finger spring plate of the sample tube holder of FIG. 1.
Figure 8:
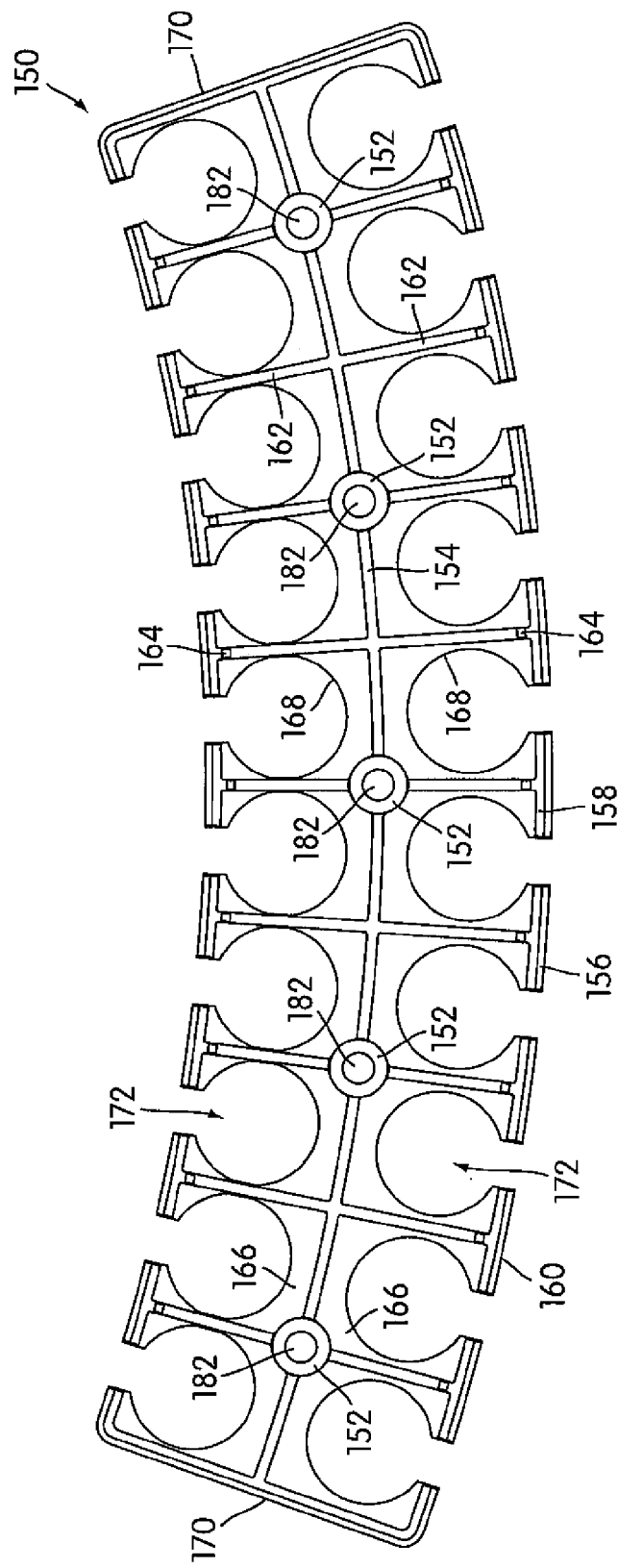
FIG. 8 is a bottom view of the spacer of FIG. 7.

Above the first finger spring plate 60 is the spacer 150, a structure which is provided to space the finger springs 100 of the first and second finger spring plates 60, 120 apart from each other to ensure a substantially vertical alignment of each sample tube 300 in the sample tube compartments 250. Misaligned sample tubes 300 could affect the penetrablity of associated sealed caps 310 or, possibly, level sensing procedures within the sample tubes. FIG. 8 shows a series of spaced-apart bosses 152 along a dividing wall 154 of the spacer 150 which register with a mated series of recesses 80 in a top surface 82 of the first finger spring plate 60. Flexing of the spacer 150 is limited by the inclusion of the mated shoulders 84, 156 about the periphery of the top surface 82 of the first finger spring plate 60 and a bottom surface 158 of a side wall 160 of the spacer. Spaced-apart partitions 162 extending radially or laterally outward from the dividing wall 154 and the bosses 152 of the spacer 150 include protuberances 164 adjacent the side wall 160 which register with receiving holes 86 in the top surface 82 of the first finger spring plate 60 to further limit flexing of the spacer. A bisecting wall 166 extending laterally or radially outward from the dividing wall 154 also contributes to the rigidity of the spacer 150. The bisecting wall 166 includes a series of spaced-apart openings 168, and each opening of the bisecting wall is coaxially aligned with a set of openings 62, 122 in the first and second finger spring plates 60, 120 and is sized to receive sample tubes 300 therethrough. (Except for the recesses 80 in the top surface 82 of the first finger spring plate 60, the first and second finger spring plates 60, 120 are substantially the same and, therefore, each is described with reference to FIGS. 5 and 6.) When the sample tube holder 10 is assembled, the dividing wall 154 and partitions 162 of the spacer 150 are in touching contact with the top surface 82 of the first finger spring plate 60, and the area above each opening 62 and generally contained within the side wall 160, the dividing wall 154 and between a pair of adjacent partitions 162 or one of the partitions and an end wall 170 of the spacer defines a chamber 172 which forms part of the sample tube compartment 250.

Figure 7:
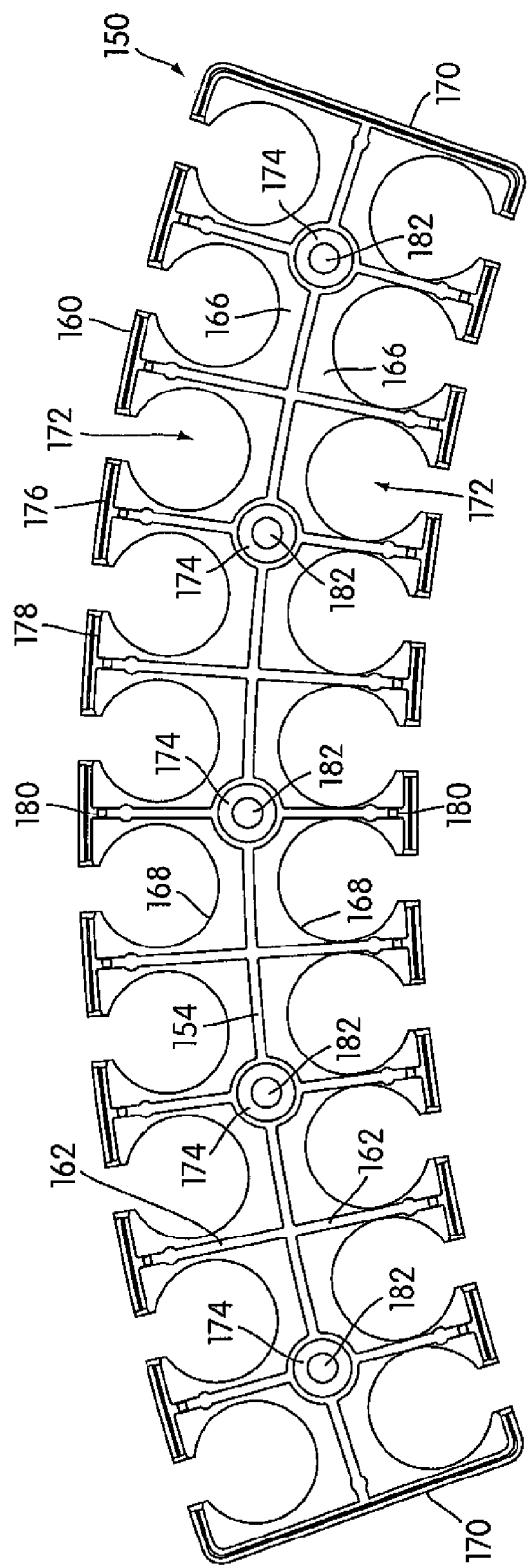
FIG. 7 is a top view of a spacer of the sample tube holder of FIG. 1.

Like the first finger spring plate 60, a series of spaced-apart bosses 126 depending from along a dividing wall 128 of the second finger spring plate register the second finger spring plate on the spacer 150 using mated recesses 174 along the dividing wall 154 of the spacer. See FIGS. 6 and 7. In addition, an upper shoulder 178 extending about a top surface 176 of the side wall 160 of the spacer 150 registers with a mated lower shoulder 130 extending about a bottom surface 132 of a side wall 134 of the second finger spring plate 120. As with the other components, partitions 136 depending from the bottom surface 124 of the second finger spring plate 120 include receiving holes 138 adjacent the side wall 134 which register with protuberances 180 extending upward from the partitions 162 in the spacer 150 adjacent the side wall 160 to limit movement of the second finger spring plate. The partitions 136, 162 and dividing walls 128, 154 of the second finger spring plate 120 and the spacer 150 are generally in touching contact when the sample tube holder 10 is fully assembled, thereby further defining the generally enclosed sample tube compartments 250. The openings 122 in the second finger spring plate 120 constitute the entry points into the sample tube compartments 250.

Figure 11:
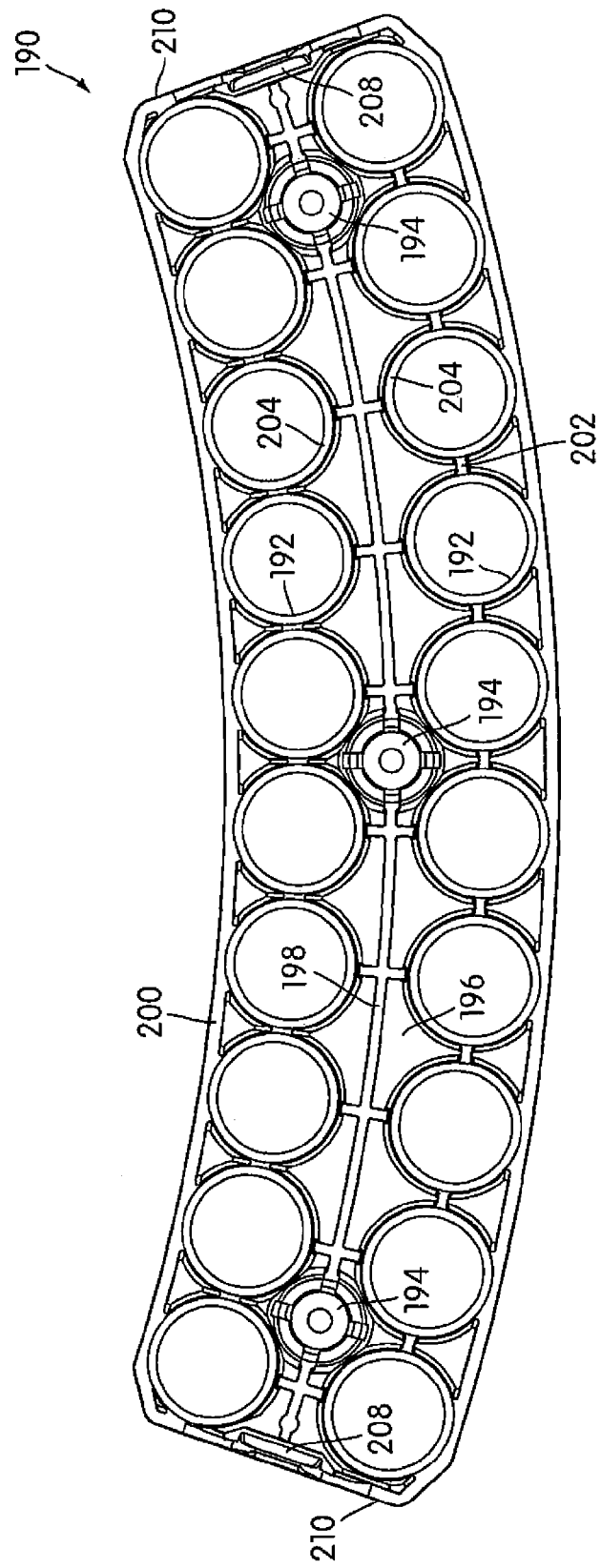
FIG. 11 is a bottom view of the guide structure of FIG. 10.

FIGS. 10 and 11 show a series of spaced-apart bosses 194 joined to a bottom surface 196 of the guide structure 190. The bosses 194 are positioned along a rib structure 198 which separates the two, parallel sets of openings 192 in the guide structure 190. One function of the bosses 194 is to register the guide structure 190 on the second finger spring plate 120 using mated recesses 140 on a top surface 142 of the second finger spring plate. The tapered openings 192 in the guide structure 190 aid in positioning at least a portion of the caps 310 within the openings when the sample tubes 300 are fully inserted into the sample tube compartments 250. Preferably, the longitudinal axes of the caps 310 deviate from the longitudinal axes of the openings 192 by no more than about 0.020 inches (0.508 mm), and the longitudinal axes of the caps deviate from the longitudinal axes of fluid transfer devices penetrating the caps by no more than about 0.10 inches (2.54 mm) when the sample tubes 300 are fully inserted into the sample tube compartments. Also, in addition to the rib structure 198, a peripheral side wall 200 and bridges 202 improve the structural rigidity of the guide structure 190 by joining rims 204 depending from the bottom surface 196 of the guide structure and circumscribing each opening 192.

Figure 13:
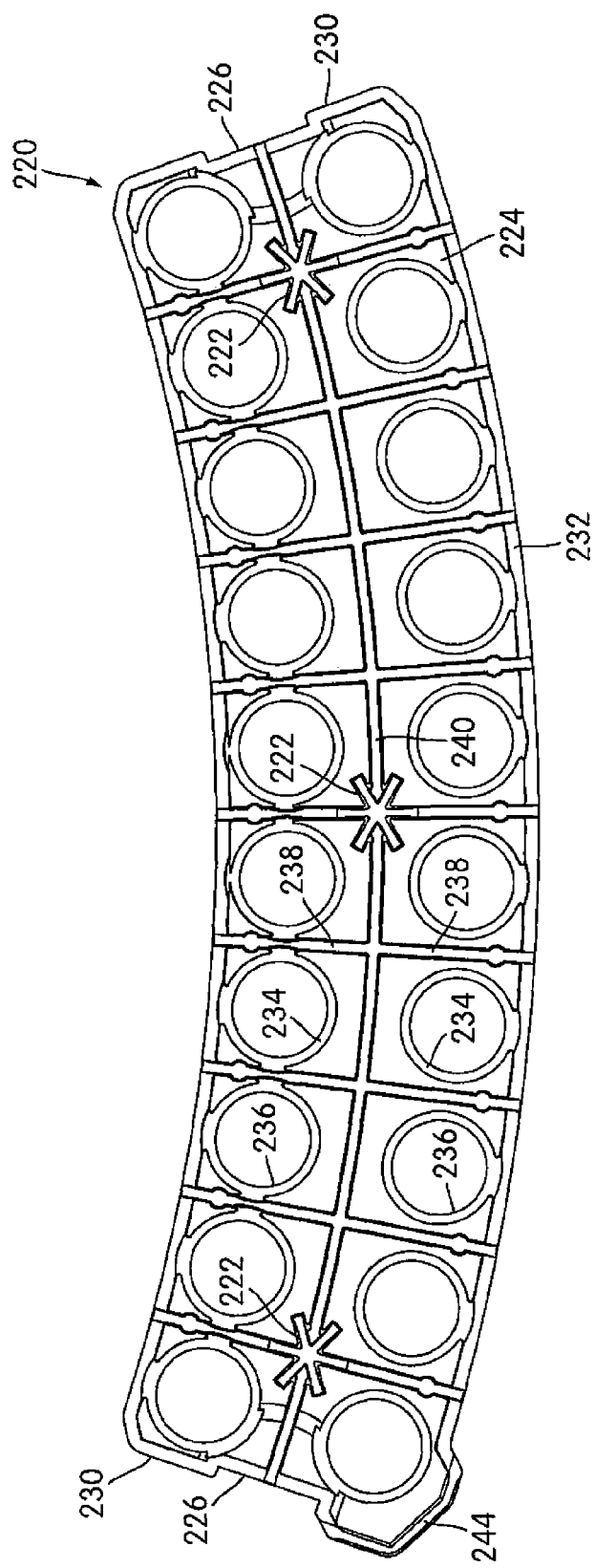
FIG. 13 is a bottom view of a retainer of the sample tube holder of FIG. 1.

FIG. 13 shows a set of spaced-apart bosses 222 depending from a bottom surface 224 of the retainer 220 which are inserted into mated recesses 206 in the guide structure 190, which are shown in FIG. 9 above the bosses 194, and serve to register the retainer on the guide structure. As the bosses 222 of the retainer 220 are inserted into the recesses 206 of the guide structure 190, a pair of latches 208 located at ends 210 of the guide structure engage a pair of corresponding notches 226 formed in a top surface 228 of the retainer 220 (collectively referred to herein as the "latch system") to releasably hold the retainer relative to the guide structure. Each latch 208 has a sloped face 212 for sliding over an end portion 230 of a side wall 232 of the retainer 220 as the retainer is joined to the guide structure 190, and a ledge 214 for engaging the top surface 228 of the retainer in the area of one of the notches 226. FIG. 2 shows a fully assembled version of the preferred sample tube holder 10 with a contained sample tube 300.

Assembly screws (not shown) inserted through through-holes 56, 88, 182, 144 in the base 30, first finger spring plate 60, spacer 150 and second finger spring plate 120 (see FIGS. 4-8), and in threading engagement with the corresponding set of bosses 194 depending from the guide structure 190 (see FIG. 10), operate to maintain these five components of the sample tube holder 10 in fixed position relative to each other. Other means for joining the components are contemplated, including ultrasonic welding or an adhesive.

To permit viewing of machine readable information 270 (e.g., bar code) that may be applied to the sample tubes 300, each sample tube compartment 250 preferably includes a vertical slot 260. As shown in FIG. 2, the slot 260 is an opening which extends through the side walls 52, 74, 160, 134 of the base 30, the first finger spring plate 60, the spacer 150 and the second finger spring plate 120. The machine readable information 270 may provide information about, for example, the contents of the sample tubes 300 or assays to be performed on such contents.

For automated applications, means may also be included for determining whether sample tubes 300 are present in the sample tube compartments 250 prior to pipetting. Such means may include a device (not shown) for interpreting machine readable information 280 (e.g., bar code) applied to the dividing wall 154 of the spacer 150 within each sample tube compartment 250, as shown in FIGS. 1 and 2. If the sample tubes 300 or their contents are opaque or sufficiently translucent to obscure the machine readable information 280 on the dividing wall, or interfering labels 270 are affixed to the sample tubes, the device should not be able to read or detect the machine readable information behind the sample tubes. Failing to read or detect machine readable information 280, the device can communicate to a computer controlling the operation of an associated automated sampling system that the sample tubes 300 are present in the sample tube compartments 250. As a result, a robotic pipettor (not shown) associated with the automated sampling system will be instructed draw a predetermined amount of sample from the sample tubes 300 within the sample tube compartments 250. But, if a sample tube compartment 250 does not contain a sample tube 300, the device will read or detect the corresponding machine readable information 280 and communicate to the computer that no sample tube 300 is present in that sample tube compartment. Accordingly, the robotic pipettor will be instructed to pass over that particular sample tube compartment 250.

The aligned sets of finger springs 100 within the sample tube compartments 250 are spaced longitudinally from each other to limit pivoting of the sample tubes 300. A plurality of finger springs 100 are arrayed about the periphery of each opening 62, 122 of the first and second finger spring plates 60, 120 to prevent the sample tubes 300 from slipping out of vertical alignment. In a particularly preferred embodiment illustrated in FIG. 6, each set of finger springs 100 includes a total of four finger springs. This number is preferred because the finger springs 100 can be equally spaced so that they do not interfere with the viewing of machine readable information 270, 280 on either the sample tubes 300 or the dividing wall 154 of the spacer 150. Alternatively, if three equally spaced finger springs 100 make up each set of finger springs, then one finger spring of a set may obstruct viewing of machine readable information 270, 280 associated with a sample tube 300 or its corresponding sample tube compartment 250.

Figure 14:
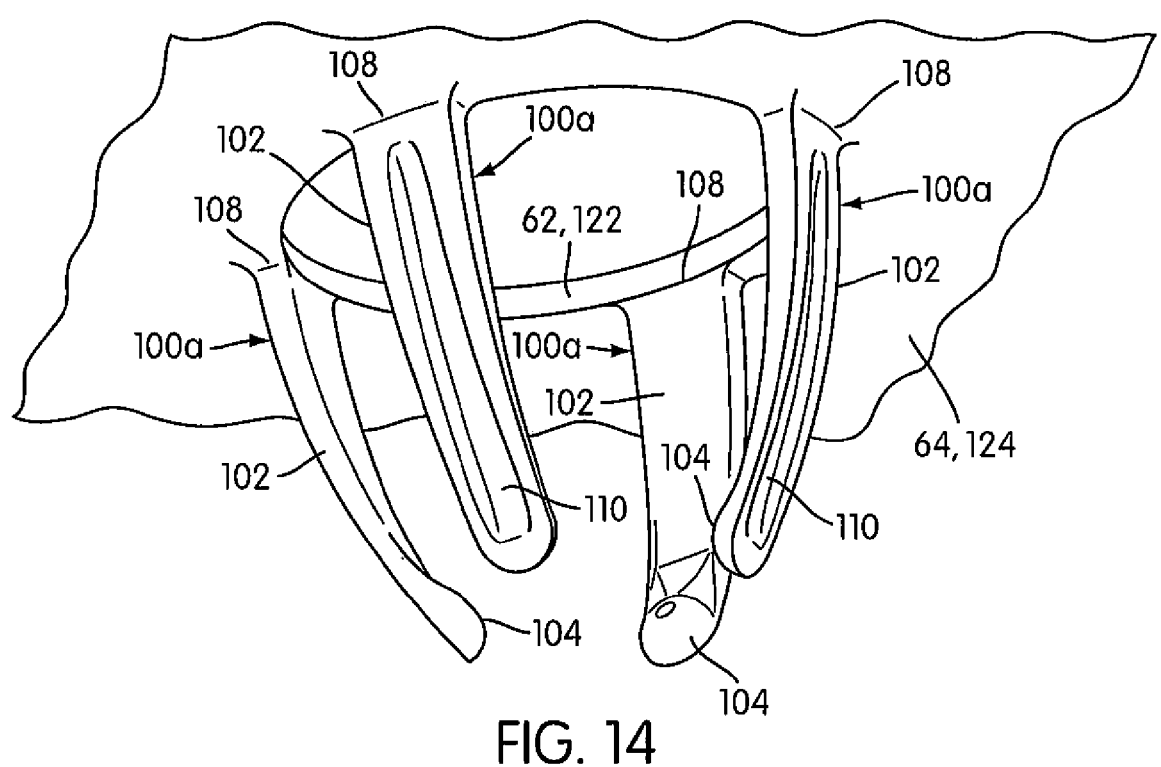
FIG. 14 is a representative, section perspective view of a preferred set of finger springs depending from a bottom surface of the finger spring plate of FIG. 6 (partitions for isolating the openings in the finger spring plate are not shown).
Figure 15:
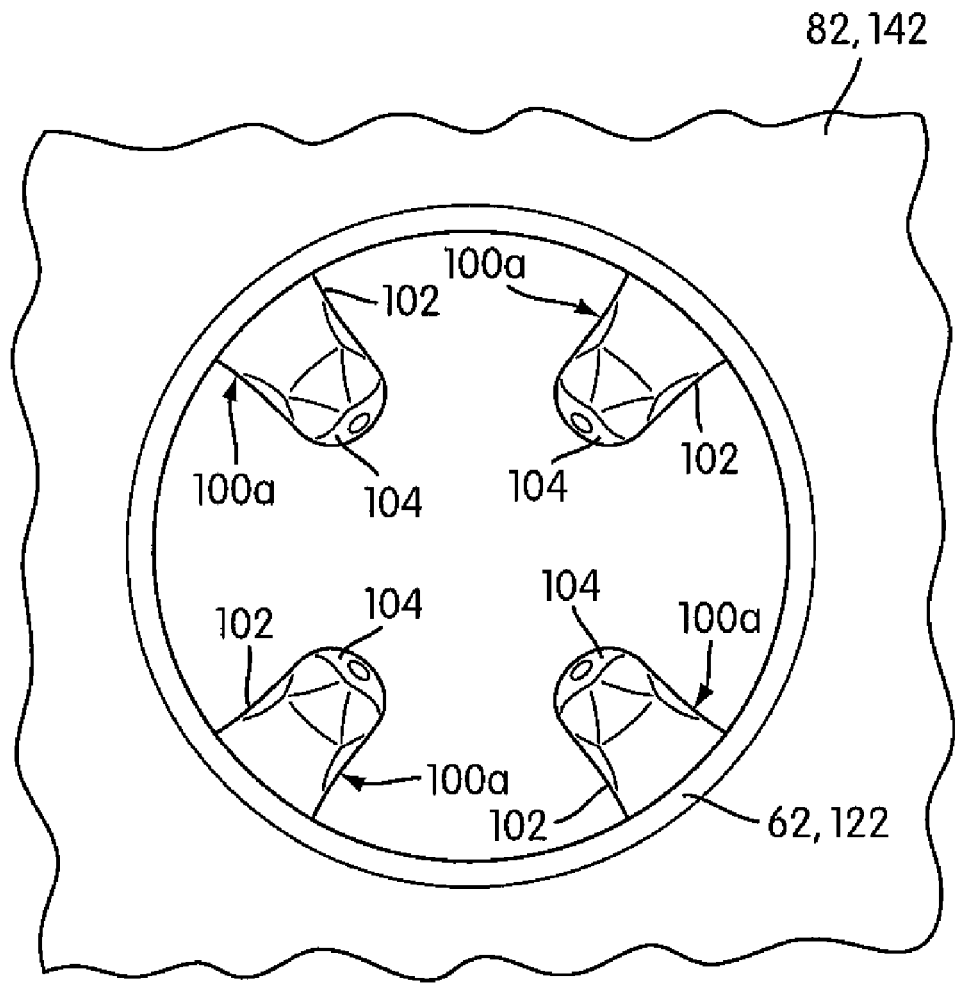
FIG. 15 is a representative, section top view of an opening in the finger spring plate of FIG. 14 (adjacent receiving holes are not shown).
Figure 16:
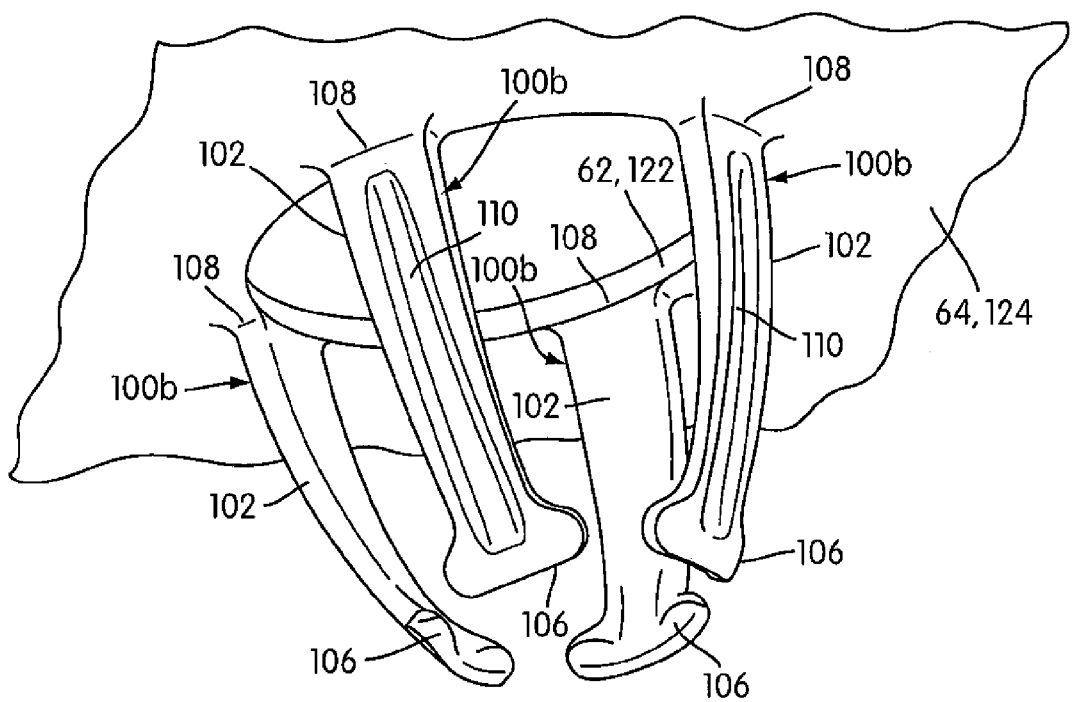
FIG. 16 is a representative, section perspective view of alternative set of finger springs depending from a bottom surface of the finger spring plate of FIG. 6 (partitions for isolating the openings in the finger spring plate are not shown).
Figure 17:
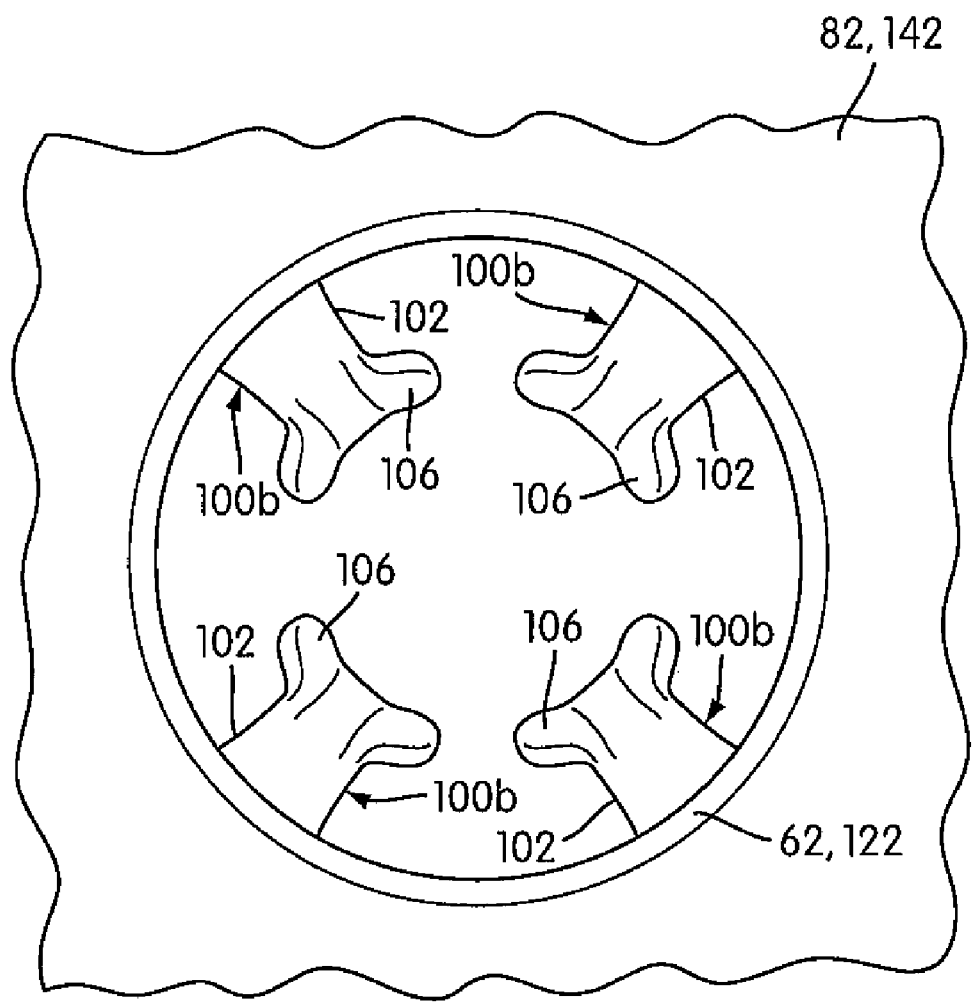
FIG. 17 is a representative, section top view of an opening in the finger spring plate of FIG. 16 (adjacent receiving holes are not shown).

As shown in FIGS. 14 and 16, each finger spring 100 includes an inwardly bowed, flexible arm 102 and a distal end 104, 106 which is in sliding, frictional contact with a sample tube 300 as it is being inserted into or withdrawn from a sample tube compartment 250. To limit the frictional contact between the distal ends 104 of the finger springs 100a and sample tubes 300, the distal ends preferably have smooth, convexly contoured single-point contacts with the sample tubes, as illustrated in FIGS. 14 and 15. In an alternative embodiment shown in FIGS. 16 and 17, distal ends 106 of the finger springs 100b are flared to provide continuous or multiple points of contact with the sample tubes 300. The distal ends 106 of this latter embodiment may more securely grip the sample tubes 300 and, accordingly, could limit the number of finger springs 100b needed in the sets of finger springs to provide substantially vertical alignment of the sample tubes.

To achieve substantially uniform bending of the flexible arms 102, the sizes of the flexible arms diminish moving in the direction of the distal ends 104, 106 from bases 108 where the finger springs 100 depend from the bottom surfaces 64, 124 of the first and second finger spring plates 60, 120. Additionally, backs of the flexible arms 102 preferably include recesses 110 to limit the material of the flexible arms and to render them more flexible upon deflection by sample tubes 300 being inserted into the sample tube compartments 250. In this way, the finger springs 100 are designed to mainly bend along the lower length of the flexible arms 102 to better distribute stress. Methods for performing elastic analysis of structures which are well known to those skilled in the art may be applied in designing finger springs to estimate the stresses and displacements finger springs will experience from applied loads, including the Finite Element Method (FEM). See, e.g., Foundations of Sold Mechanics, Y. C. Fung, 1965, Prentice-Hall, ISBN 0-13-329912-0; Advanced Strength and Applied Elasticity, A. C. Ugural and S. K. Fenster, 1975, Elsevier, ISBN 0-444-00160-3; and Formulas for Stress and Strain ($5^{th}$ Edition), R. J. Roark and W. C. Young, 1975, McGraw-Hill, ISBN 0-07-053031-9. Each of the foregoing references is hereby incorporated by reference herein.

The finger springs 100 of the present invention may be of the same or different sizes and shapes, provided that at least a plurality of the finger springs in a set of finger springs are in frictional contact with the sample tubes 300 inserted into the sample tube compartments 250 and maintain those sample tubes in substantially vertical orientations. In certain embodiments, only a single set of finger springs 100 may be needed in the sample tube compartments 250 to hold and maintain the sample tubes 300 in substantially vertical orientations. This might be the case, for example, where the openings 192 in the guide structure 190 substantially limit lateral movement at the open or capped ends of the sample tubes 300. The finger springs 100 are preferably sized and oriented to accommodate sample tubes of varying diameters. If the sample tube holders 10 of the present invention are to be used for one sized sample tube 300, then slots conforming to the dimensions of the sample tubes 300, or other fixed means, may be substituted for the finger springs 100 to hold the sample tubes 300 in substantially vertical orientations in the sample tube compartments 250. See, e.g., Sevigny et al., "Sample Carrier Having Sample Tube Blocking Means and Drip Shield for Use Therewith," U.S. Patent Publication No. US-2003-0215365-A1, the contents of which are hereby incorporated by reference herein.

After sample tubes 300 are inserted into the sample tube compartments 250, the retainer 220 is secured to the guide structure 190 using the latch system 208, 226 described above. When caps 310 have been tightened onto the receptacles 320, the caps are preferably no more than about a quarter-turn from contacting rims 234 encircling openings 236 in the retainer 220 on the bottom surface 224 of the retainer. See FIGS. 2 and 13. The openings 236 in the retainer 220 are coaxially aligned with the openings 192 in the guide structure 190 and are smaller in diameter than the caps 310 of the sample tubes 300 beneath them. The openings 236 in the retainer 220 are large enough to allow the non-interfering passage a fluid transfer device, such as a pipette tip, but are small enough to block the upward movement of a sample tube 300 should the retaining force of a cap 310 on a fluid transfer device exceed the retaining force of the finger springs 100 on the sample tube. The secured retainer 220 can preferably tolerate an upward force of at least 3 pounds (13.34 N).

As shown in FIG. 13, a series of partitions 238 extend laterally or radially outward from a dividing wall 240 and downward from the bottom surface 224 of the retainer 220. When the retainer 220 is engaged by the guide structure 190, the partitions 238 and dividing wall 240 of the retainer are generally in touching contact with a top surface 216 of the guide structure. In this way, the caps 310 of sample tubes 300 contained within the sample tube holder 10 are isolated from each other, thereby limiting opportunities for cross-contamination. Rims 242 encircling each opening 236 on the top surface 228 of the retainer 220 also reduce the chance for cross-contamination by blocking the flow of fluids present on the top surface of the retainer. Such fluids may include sample material which becomes dislodged from a fluid transfer device.

For identification purposes, the retainer 220 also preferably includes structure 244 for accommodating machine readable information 290 (e.g., scannable bar code). As shown in FIG. 1, the structure 244 can extend from an end portion 230 of the side wall 232 where it can be viewed by a device for interpreting machine readable information (e.g., bar code scanner). Relevant information which may be provided by the machine readable information 290 includes, for example, an identification of the sample tube holder 10, types of sample material held by the sample tube holder, and/or the tests to be performed on the sample materials.

Figure 18:
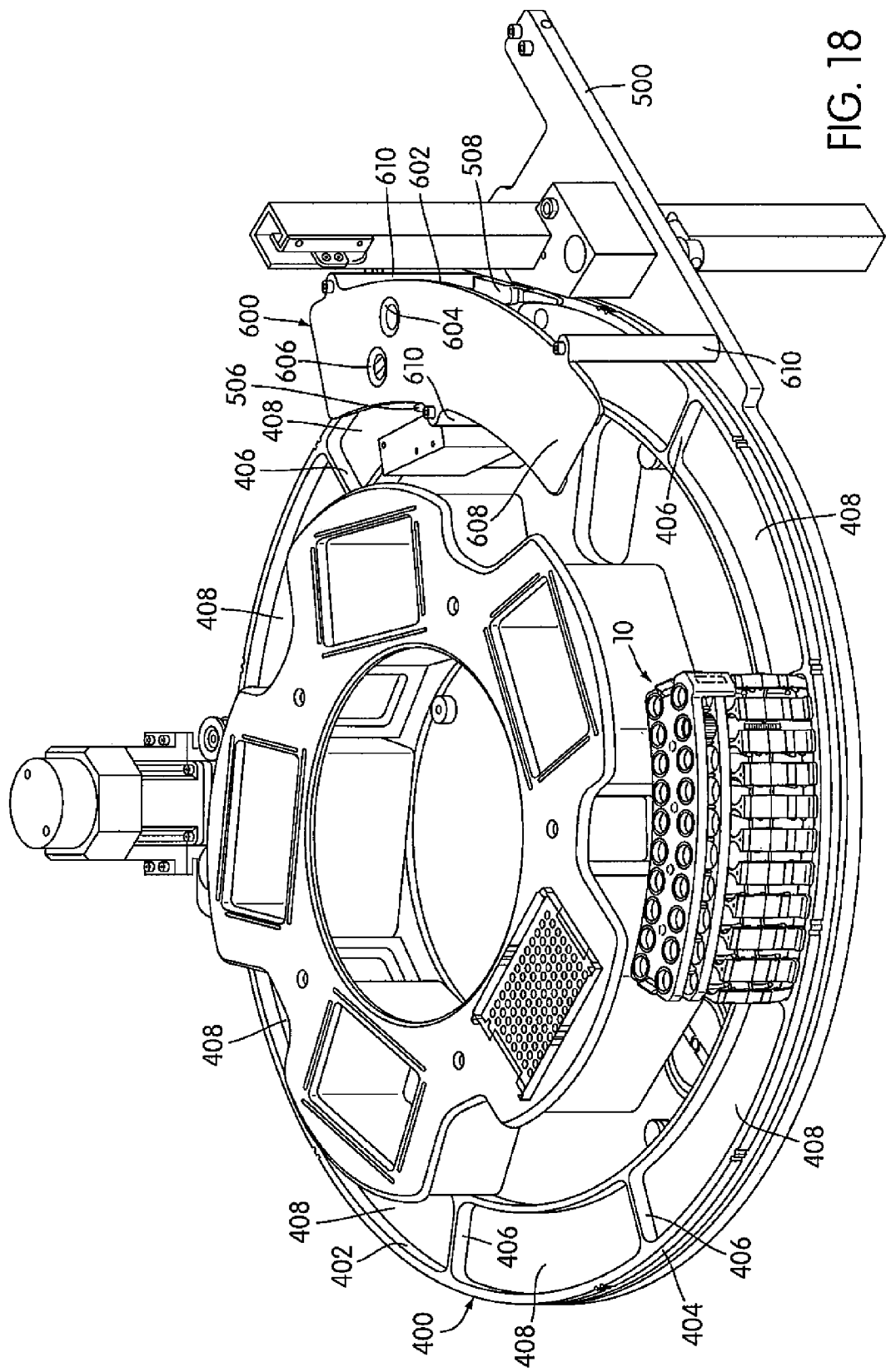
FIG. 18 shows the sample tube holder of FIG. 1 being transported on a carousel.

The base 30 of the sample tube holder 10 may be adapted for use with a conveyor for transporting the sample tube holder, such as a carousel for holding and rotating a plurality of sample tube holders within an automated sampling system. One such carousel 400 is disclosed by Ammann et al. in U.S. Pat. No. 6,335,166 and is illustrated in FIG. 18. This particular carousel 400 is formed of milled, unhardened aluminum and includes an annular trough 402 about the periphery of a ring 404 and a plurality of raised, radially extending dividers 406. The dividers 406 divide the trough 402 into nine arcuate sample tube holder receiving wells 408 which can be configured to accommodate the sample tube holders 10 of the present invention. The individual sample tube holder receiving wells 408 are dimensioned to maintain the sample tube holders 10 in an upright position as sample tubes 300 held by the sample tube holders are indexed under a robotic pipettor (not shown) for retrieving sample material for analysis. To track individual sample tube holders 10 on the carousel 400, machine readable information 290 (e.g., scannable bar code) can be provided to the structure 244 of the retainer 220, as described above. For the sample tube holder 20 shown in FIG. 3, the machine readable information may be applied to, for example, one of the end surfaces 170 of the spacer 150.

Figure 12:
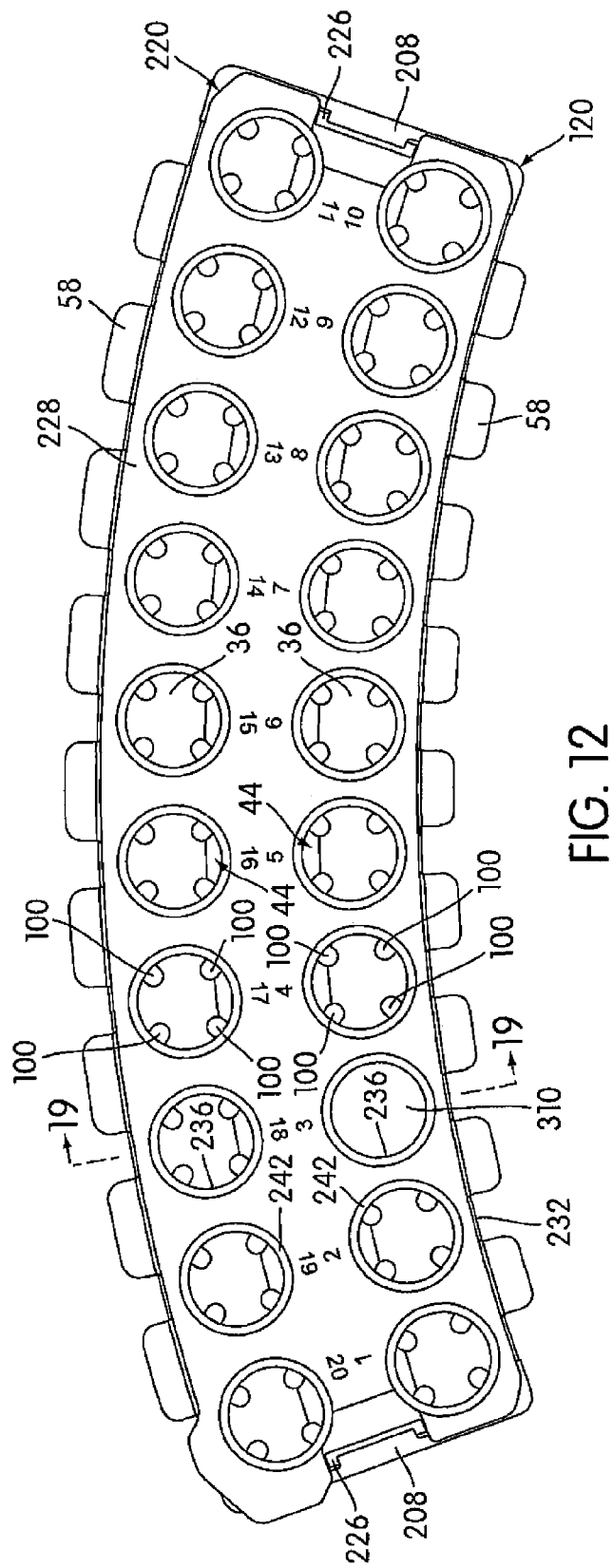
FIG. 12 is a top plan view of the sample tube holder of FIG. 1.
Figure 19:
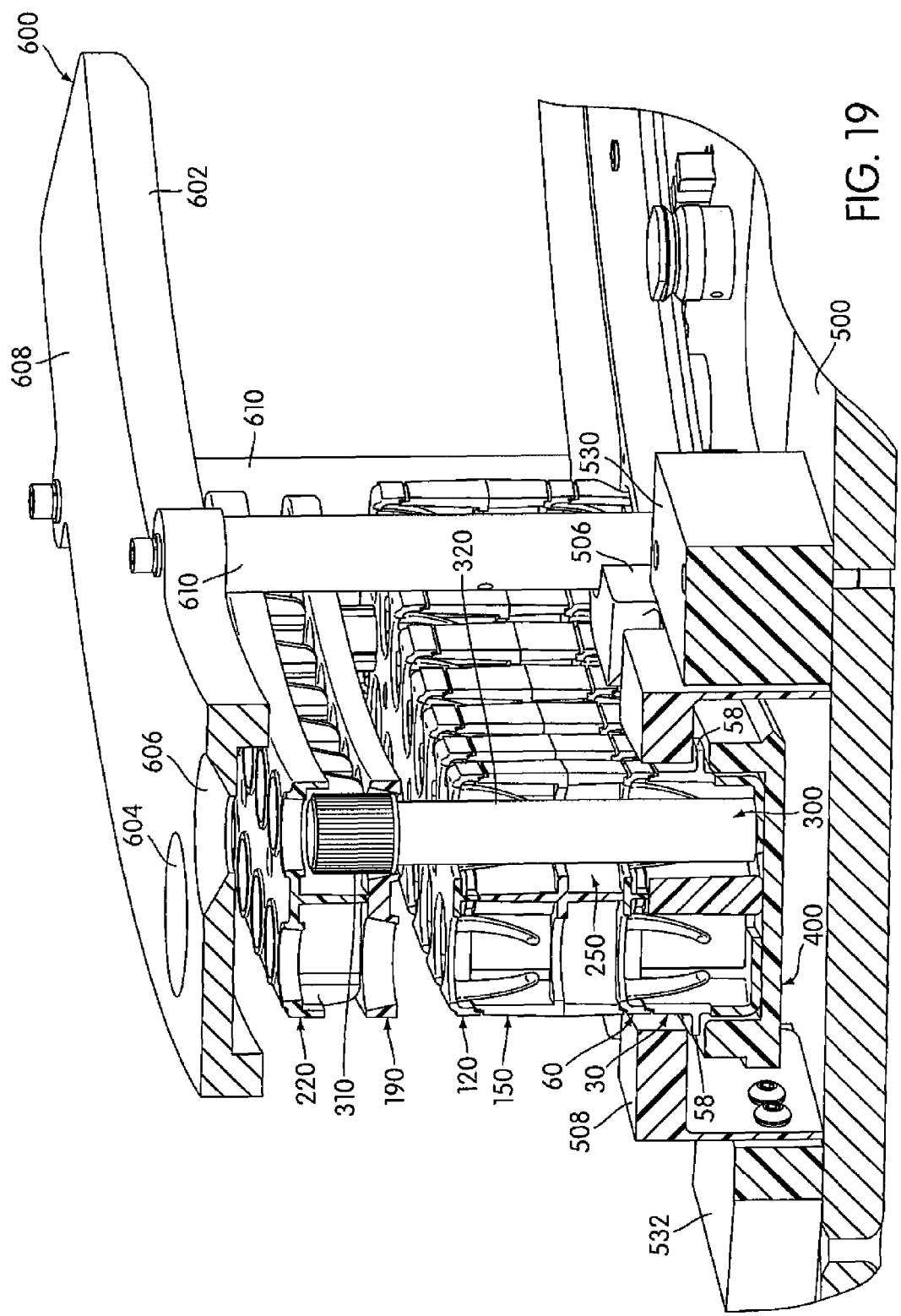
FIG. 19 is a perspective section end view of the sample tube holder of FIG. 12, taken along the 19-19 line thereof, being transported under a drip shield adjacent hold-downs fixed to a stationary surface shown in FIG. 18.
Figure 20:
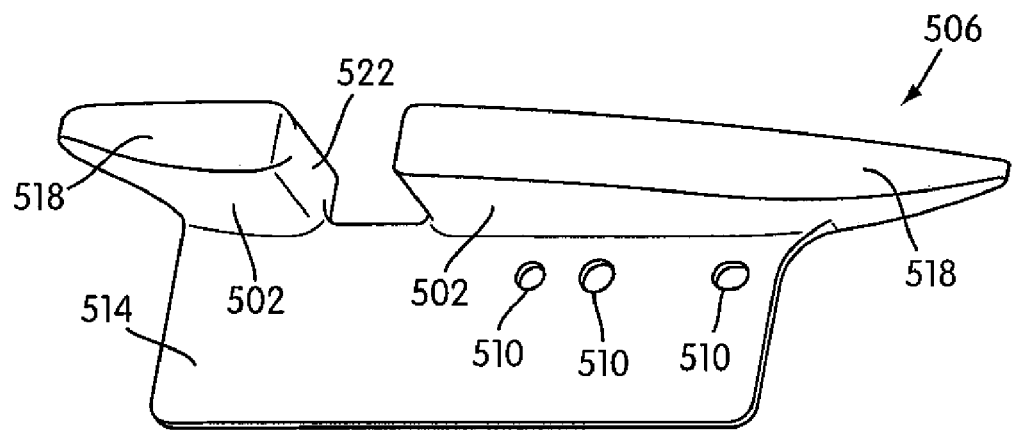
FIG. 20 is a front perspective view of an inner hold-down shown in section perspective view in FIG. 19.
Figure 21:
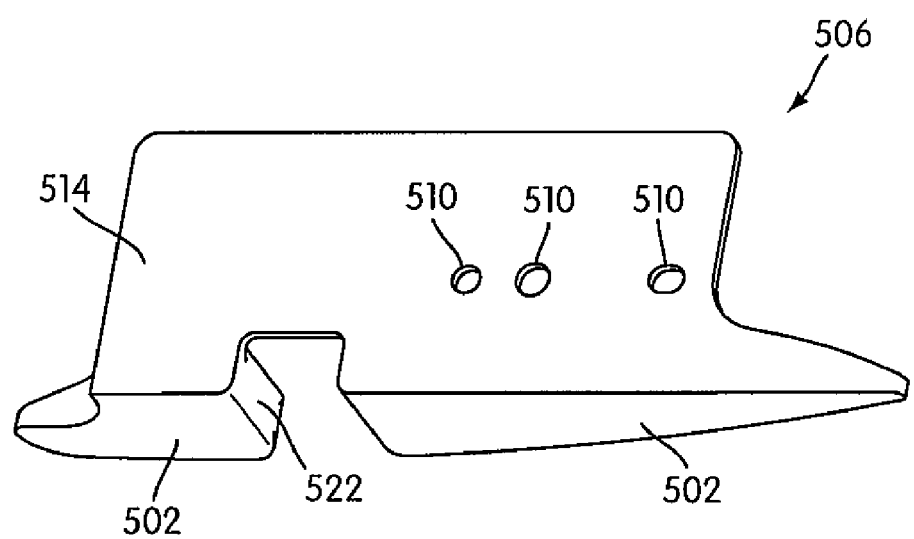
FIG. 21 is a rear perspective view of the inner hold-down of FIG. 20.
Figure 22:
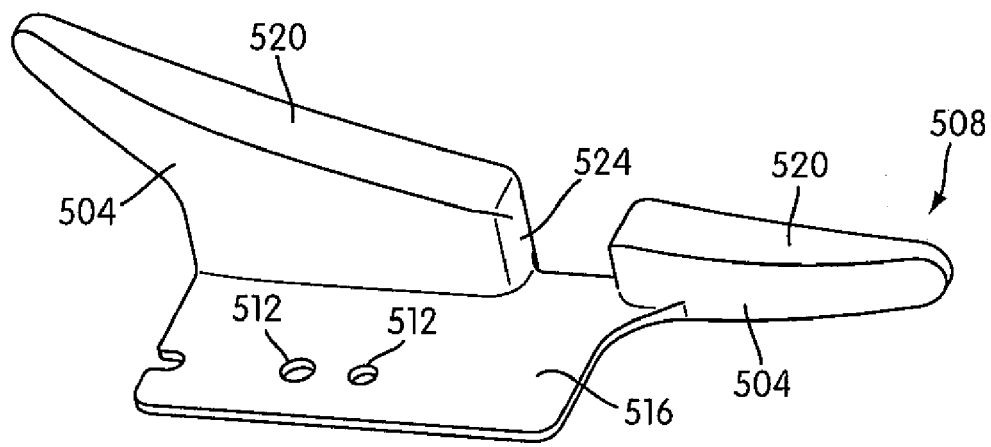
FIG. 22 is a front perspective view of an outer hold-down shown in section perspective view in FIG. 19.
Figure 23:
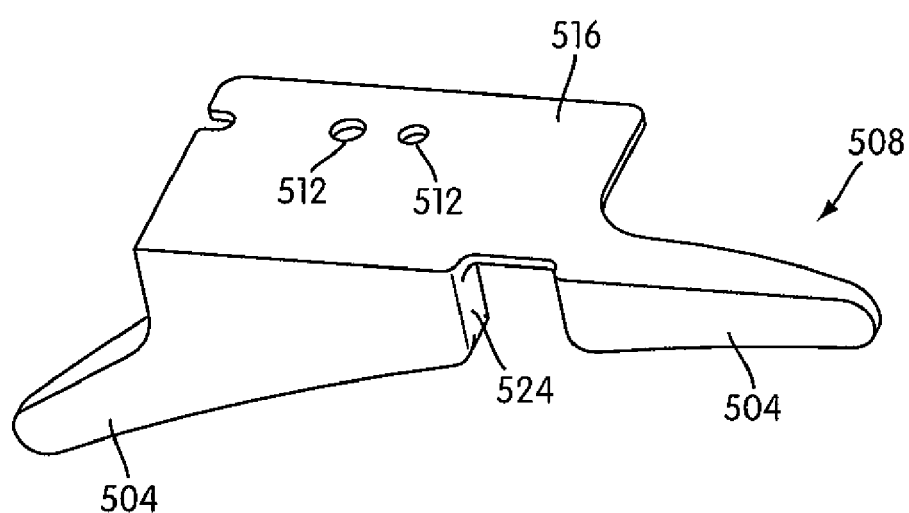
FIG. 23 is a rear perspective view of the outer hold-down of FIG. 22.

To maintain the sample tube holders 10 in the sample tube holder receiving wells 408 of the carousel 400, or other such conveyor, it is preferable for the sample tube holders to include a tab or series of tabs 58 which extend laterally outward from the side wall 52 of the base 30, as shown in FIGS. 4 and 12. FIG. 19 shows that the tabs 58 are sized and arranged so that they will engage fin structures 502, 504 extending laterally inward from inner and outer hold-downs 506, 508 fixed to mounting blocks 530, 532 secured to a stationary surface 500 adjacent the carousel 400 in a pipetting station if the sample tube holder 10 is vertically lifted, thereby preventing sample tube holders from being extracted from the sample tube holder receiving wells 408 during pipetting procedures. Holes 510, 512 in face plates 514, 516 of the hold-downs 506, 508 are used to screw the hold-downs to the mounting blocks 530, 532, although other attachment means are possible. In preferred embodiments shown in FIGS. 20-23, the fin structures 502, 504 of the hold-downs 506, 508 have curved end surfaces 518, 520 to accommodate the curvilinear shape of the preferred sample tube holder 10, but could have flat end surfaces if the sample tube holder had, for example, a rectilinear shape and traveled in a rectilinear as opposed to a rotational motion on a conveyor. The hold-downs 506, 508 are preferably made of forged aluminum and include a cut-out 522, 524 to permit bar code scanning of labels 270 affixed to the sample tubes 300. Without the tabs 58 and hold-downs 506, 508, extraction of a sample tube holder 10 might occur if the material of a cap 310 penetrated by a fluid transfer device exerted a retention force on the fluid transfer device (e.g., pipette tip) which was greater than the combined retention forces of the finger springs 100 and the retainer 220 on the sample tube 300.

Sample tube holders 10 of the present invention can be used in combination with a device for protecting sample tubes 300 during sampling procedures to further limit opportunities for cross-contamination. As shown in FIGS. 18 and 19, this device is preferably a drip shield 600 having a cover plate 602 which creates a canopy over the sample tube holders 10 positioned beneath it. A pair of chamfered, spaced-apart openings 604, 606 in the drip shield 600 provide fluid transfer devices with non-interfering access to parallel sets of aligned sample tubes 300 centered beneath the openings. The drip shield 600 can advantageously function to catch material, such as hanging droplets, which becomes dislodged from fluid transfer devices during sample transferring procedures. While the chamfered openings 604, 606 are particularly useful for re-directing misaligned fluid transfer devices, rims (not shown) encircling the openings 604, 606 on a top surface 608 of the drip shield 600 could serve to impede fluid collected on the cover plate 602 from draining into the sample tubes 300. Mounting posts 610 may be used to secure the drip shield 600 to the stationary surface 500 adjacent the carousel 400. The drip shield 600 is preferably made of a substantially non-conductive plastic, such as acrylonitrile-butadiene-styrene (ABS) available from GE Plastics of Pittsfield, Mass. as Cycolac® MG47.

While the sample tube holders of the present invention have been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A sample tube holder comprising:
   a base;
   a first sample tube holding structure positioned above and structurally interrelated to the base, the first sample tube holding structure having a series of openings and a set of spaced-apart finger springs depending inwardly from about each opening, each set of finger springs being configured and arranged to frictionally hold a sample tube therebetween;
   a second sample tube holding structure spaced from and structurally interrelated to the first sample tube holding structure, the second sample tube holding structure having a series of openings and a set of spaced-apart finger springs depending inwardly from about each opening, each set of finger springs being configured and arranged to frictionally hold a sample tube therebetween, and the openings of the first sample tube holding structure being coaxially aligned with the openings of the second sample tube holding structure;
   a guide structure positioned above and structurally interrelated to the second sample tube holding structure, the guide structure having a series of openings, each opening of the guide structure being sized to receive a sample tube therethrough, and each opening of the guide structure being coaxially aligned with an aligned set of openings in the first and second sample tube holding structures, wherein the guide structure comprises a generally planar member having a top surface; and
   a retainer that is releasably engaged by the guide structure, the retainer having a series of openings coaxially aligned with the openings in the guide structure, each opening in the retainer being sized to allow non-interfering passage a fluid transfer device therethrough, and each opening in the retainer being sized to block the passage of a sample tube therethrough, wherein the retainer comprises a bottom surface and a series of partitions depending therefrom, such that the partitions are generally in touching contact with the top surface of the guide structure adjacent each opening of the guide structure.

2. The sample tube holder of claim 1, wherein distal ends of the finger springs are convexly shaped.

3. The sample tube holder of claim 1, wherein each of the first and second sample tube holding structures comprises a generally planar member having a bottom surface, the finger springs depending from the bottom surfaces of the generally planar members about the periphery of each opening.

4. The sample tube holder of claim 1 further comprising a spacer for joining the first sample tube holding structure to the second sample tube holding structure, the spacer defining a series of chambers, each chamber being aligned with and extending between a set of aligned openings in the first and second sample tube holding structures, and each chamber being sized to receive a sample tube therein.

5. The sample tube holder of claim 4, wherein each chamber has a slot formed therein to permit viewing of machine readable information on an opposed surface of the chamber or a sample tube contained in the chamber.

6. The sample tube holder of claim 4, wherein the series of openings in each of the first and second sample tube holding structures is comprised of two sets of generally parallel openings, the two sets of generally parallel openings being separated from each other by a dividing wall in the spacer.

7. The sample tube holder of claim 1, wherein the base includes a series of spaced, upwardly extending partitions which divide the base into a plurality of sample tube receiving wells, each well being sized to receive the distal end of a sample tube, and each well being positioned beneath one of the chambers and a set of aligned openings in the first and second sample tube holding structures to collectively form a sample tube compartment.

8. The sample tube holder of claim 7, wherein the sample tube holder has a curvilinear shape.

9. The sample tube holder of claim 1, wherein the base has a pair of opposed end walls and a pair of opposed sidewalls, each of the sidewalls having one or more horizontally arranged tabs extending laterally therefrom, the tabs being sized and arranged to operatively engage hold-downs adjacent a sample tube holder conveyor of an automated sampling system to limit vertical movement of the sample tube holder.

10. The sample tube holder of claim 1, wherein the sample tube holder includes at least one sample tube frictionally held by the finger springs of an aligned set of openings in the first and second sample tube holding structures.

11. The sample tube holder of claim 1, wherein the openings of the guide structure are inwardly tapered.

12. The sample tube holder of claim 1, wherein the guide structure includes upwardly extending latches that releasably engage the retainer.

13. The sample tube holder of claim 12, wherein the retainer comprises a generally planar member having a top surface, the top surface including notches that are releasably engaged by the latches, each latch having a sloped face and a ledge that engages one of the notches in the top surface of the retainer.

14. The sample tube holder of claim 13, wherein the top surface of the retainer further comprises a rim extending about each opening thereof.

15. The sample tube holder of claim 1, wherein the series of openings in the retainer is comprised of two sets of generally parallel openings, the two sets of generally parallel openings being separated from each other by a dividing wall depending from the bottom surface of the retainer.

16. The sample tube holder of claim 4, wherein the base includes a series of spaced, upwardly extending partitions which divide the base into a plurality of sample tube receiving wells, each well being sized to receive the distal end of a sample tube, and each well being positioned beneath one of the chambers and a set of aligned openings in the first and second sample tube holding structures to collectively form a sample tube compartment.

17. A sample tube holder comprising:
a base defining a series of sample tube compartments for receiving and holding a plurality of sample tubes in substantially upright orientations;
a guide structure positioned above and structurally interrelated to the base, the guide structure having a series of openings, each opening of the guide structure being sized to receive a sample tube therethrough, and each opening of the guide structure being aligned with one of the sample tube compartments, wherein the guide structure comprises a generally planar member having a top surface; and
a retainer that is releasably engaged by the guide structure, the retainer having a series of spaced openings coaxially aligned with the openings in the guide structure, each opening in the retainer being sized to allow non-interfering passage a fluid transfer device therethrough, and each opening in the retainer being sized to block the passage of a sample tube therethrough, wherein the retainer comprises a bottom surface and a series of partitions depending therefrom, such that the partitions are generally in touching contact with the top surface of the guide structure adjacent each opening of the guide structure.

18. The sample tube holder of claim 17, wherein each sample tube compartment comprises a slot sized to receive and hold a sample tube in a substantially upright orientation.

19. The sample tube holder of claim 17, wherein each sample tube compartment comprises a set of downwardly depending finger springs, the finger springs being configured and arranged to frictionally hold a sample tube therebetween.

20. The sample tube holder of claim 17, wherein the guide structure includes upwardly extending latches that releasably engage the retainer.

21. The sample tube holder of claim 17, wherein the sample tube holder includes a sample tube held by one of the sample tube compartments, and wherein the sample tube has a cap having a closed side wall that is at least partially contained within a closed wall defining one of the openings of the guide structure, the opening being aligned with the sample tube compartment.

* * * * *